US012194000B2

(12) United States Patent
Weiner

(10) Patent No.: US 12,194,000 B2
(45) Date of Patent: Jan. 14, 2025

(54) OPTIMIZED SYNTHETIC CONSENSUS IMMUNOGENIC COMPOSITIONS TARGETING CHONDROITIN SULFATE PROTEOGLYCAN 4 (CSPG4)

(71) Applicant: THE WISTAR INSTITUTE OF ANATOMY AND BIOLOGY, Philadelphia, PA (US)

(72) Inventor: David Weiner, Merion, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 948 days.

(21) Appl. No.: 17/264,545

(22) PCT Filed: Aug. 1, 2019

(86) PCT No.: PCT/US2019/044619
§ 371 (c)(1),
(2) Date: Jan. 29, 2021

(87) PCT Pub. No.: WO2020/028635
PCT Pub. Date: Feb. 6, 2020

(65) Prior Publication Data
US 2021/0308243 A1    Oct. 7, 2021

Related U.S. Application Data

(60) Provisional application No. 62/713,123, filed on Aug. 1, 2018.

(51) Int. Cl.
*A61P 35/00* (2006.01)
*A61K 9/00* (2006.01)
*A61K 39/00* (2006.01)
*C12N 15/63* (2006.01)

(52) U.S. Cl.
CPC .... *A61K 39/001174* (2018.08); *A61K 9/0009* (2013.01); *A61P 35/00* (2018.01); *C12N 15/63* (2013.01); *A61K 2039/53* (2013.01); *A61K 2039/572* (2013.01); *A61K 2039/876* (2018.08)

(58) Field of Classification Search
CPC ........ A61K 39/001174; A61K 2039/53; A61K 2039/572; A61K 2039/876; A61P 35/00; C12N 15/63
See application file for complete search history.

(56) References Cited

U.S. PATENT DOCUMENTS 7,169,894 B2 * 1/2007 Martin ................ G01N 33/6803
435/7.1

FOREIGN PATENT DOCUMENTS

WO    WO-9713855 A1 *    4/1997    ......... C07K 14/4748
WO    WO-2011039126 A1 *  4/2011    ........... A61K 39/395

OTHER PUBLICATIONS

Flingai et al., Synthetic DNA vaccines: improved vaccine potency by electroporation and co-delivered genetic adjuvants, 2013, Frontiers in Immunology, vol. 4, Article 354, pp. 1-10 (Year: 2013).*
Yu et al., DNA vaccines for cancer too, 2006, Cancer Immunology, Immunotherapy, vol. 55, pp. 119-130 (Year: 2006).*
Albershardt et al., Checkpoint inhibitors synergize with therapeutic platforms, ZVex and GLAAS by enhancing lentiviral vector-induced tumor-specific immunity and adjuvant-mediated anti-tumor efficacy, 2015, Journal of Immunotherapy of Cancer, vol. 3, Supplement 2, p. 1 (Year: 2015).*
Zeng et al., Identifying Stabilizers of Plasmid DNA for Pharmaceutical Use, 2010, Journal of Pharmaceutical Sciences, vol. 100, No. 3, pp. 904-914 (Year: 2010).*
Rolih et al., CSPG4: a prototype oncoantigen for translational immunotherapy studies, 2017, Journal of Translational Medicine, vol. 15, Issue 151, pp. 1-14 (Year: 2017).*
Uniprot, Q6UVK1; CSPG4_HUMAN, 2005, retrieved from: https://www.uniprot.org/uniprotkb/Q6UVK1/entry (Year: 2005).*
"*Homo sapiens* melanoma chondroitin sulfate proteoglycan (CSPG4) mRNA", Nucleotide, (Jul. 12, 2004), Database accession No. AY359468, URL: NCBI, XP055682835. 4 pages.
Barutello et al., "Strengths and Weaknesses of Pre-Clinical Models for Human Melanoma Treatment: Dawn of Dogs' Revolution for Immunotherapy", Int J Mol Sci., (Mar. 10, 2018), vol. 19, No. 3, pp. 1-21, XP055682846.
Burns et al., "A high molecular weight melanoma-associated antigen-specific chimeric antigen receptor redirects lymphocytes to target human melanomas." Cancer Res 2010, 70(8):3027-3033.
Campoli et al., "Functional and clinical relevance of chondroitin sulfate proteoglycan 4." Adv Cancer Res 2010, 109:73-121.
Ferraro B, et al., "Co-delivery of PSA and PSMA DNA vaccines with electroporation induces potent immune responses." Hum Vaccin 2011, 7 Suppl:120-127.
Geldres C, et al., "T lymphocytes redirected against the chondroitin sulfate proteoglycan-4 control the growth of multiple solid tumors both in vitro and in vivo." Clin Cancer Res 2014, 20(4):962-971.
Kim, "Anti-tumor effect induced by both DNA vaccine and oncolytic adenovirus expressing multi-target genes related to immunity in malignant melanoma", Doctoral Dissertation, (20140000), p. 12, URL: https://ir.ymlib.yonsei.ac.kr/bitstream/22282913/146052/1/T013380.pdf, (Nov. 20, 2019), XP055682840.
Pellegatta S, et al., "Constitutive and TNFalpha-inducible expression of chondroitin sulfate proteoglycan 4 in glioblastoma and neurospheres: Implications for CAR-T cell therapy." Sci Transl Med 2018, 10(430).

(Continued)

*Primary Examiner* — Jeffrey Stucker
*Assistant Examiner* — Brittney E Donoghue
(74) *Attorney, Agent, or Firm* — Riverside Law LLP

(57) ABSTRACT

Provided herein is an immunogenic composition comprising a synthetic consensus antigen to chondroitin sulfate proteoglycan 4 (CSPG4) protein which is abundant in many cancers. Also disclosed herein is a method of treating a tumor associated pathology in a subject in need thereof, by administering the immunogenic composition to the subject.

20 Claims, No Drawings
Specification includes a Sequence Listing.

(56) References Cited

OTHER PUBLICATIONS

Piras LA, et al., "Prolongation of survival of dogs with oral malignant melanoma treated by en bloc surgical resection and adjuvant CSPG4-antigen electrovaccination." Vet Comp Oncol 2017, 15(3):996-1013.
Riccardo et al., "CSPG4-specific immunity and survival prolongation in dogs with oral malignant melanoma immunized with human CSPG4 DNA", Clin Cancer Res., (20140000), vol. 20, No. 14, doi: 10.1158/1078-0432.CCR-13-3042, pp. 3753-3762, XP055288899.
Rivera Z, et al., "CSPG4 as a target of antibody-based immunotherapy for malignant mesothelioma." Clin Cancer Res 2012, 18(19):5352-5363.
Shin TH, et al., "Induction of robust cellular immunity against HPV6 and HPV11 in mice by DNA vaccine encoding for E6/E7 antigen." Hum Vaccin Immunother 2012, 8(4):470-478.
Wang X, et al., "CSPG4 protein as a new target for the antibody-based immunotherapy of triple-negative breast cancer." J Natl Cancer Inst 2010, 102(19):1496-1512.
Yan J, et al., "Highly optimized DNA vaccine targeting telomerase reverse transcriptase stimulates potent antitumor immunity." Cancer immunology research 2013, 1(3):179-189.
Yan J, et al., "Enhanced cellular immune responses elicited by an engineered HIV-1 subtype B consensus-based envelope DNA vaccine." Molecular therapy : the journal of the American Society of Gene Therapy 2007, 15 (2):411-421.
Yan J, et al., Induction of antitumor immunity in vivo following delivery of a novel HPV-16 DNA vaccine encoding an E6/E7 fusion antigen. Vaccine 2009, 27(3):431-440.
Yang et al., "Melanoma chondroitin sulfate proteoglycan enhances FAK and ERK activation by distinct mechanisms", J Cell Biol., (20040000), vol. 165, No. 6, pp. 881-891.

\* cited by examiner

OPTIMIZED SYNTHETIC CONSENSUS IMMUNOGENIC COMPOSITIONS TARGETING CHONDROITIN SULFATE PROTEOGLYCAN 4 (CSPG4)

CROSS-REFERENCE TO RELATED APPLICATIONS

This application is a 35 U.S.C. § 371 national phase application from International Application PCT/US19/44619, filed Aug. 1, 2019, which claims priority to U.S. Provisional Application No. 62/713,123, filed Aug. 1, 2018, the disclosures of which are hereby incorporated by reference in their entireties.

TECHNICAL FIELD

The present invention relates to immunogenic compositions targeting Chondroitin sulfate proteoglycan 4 (CSPG4), and methods of administering the immunogenic compositions.

BACKGROUND OF THE INVENTION

Chondroitin sulfate proteoglycan 4 (CSPG4), a transmembrane glycoprotein with functional roles in tumor migration, invasion, angiogenesis, and metastasis, has emerged as a promising tumor antigen target due to its overexpression in several solid cancer types and limited expression in normal tissue.

Thus, there is a need in the art for the development of vaccines directed at CSPG4 capable of breaking tolerance. The present invention satisfies this unmet need.

SUMMARY OF THE INVENTION

In one embodiment, the invention relates to an immunogenic composition comprising a nucleic acid molecule, wherein the nucleic acid molecule encodes a peptide comprising an amino acid sequence of a) an amino acid sequence having at least about 90% identity over an entire length of the amino acid sequence selected from the group consisting of SEQ ID NO:2 and SEQ ID NO:4, b) an immunogenic fragment comprising at least about 90% identity over at least 60% of the amino acid sequence selected from the group consisting of SEQ ID NO:2 and SEQ ID NO:4, c) the amino acid sequence selected from the group consisting of SEQ ID NO:2 and SEQ ID NO:4, or d) an immunogenic fragment comprising at least 60% of the amino acid sequence selected from the group consisting of SEQ ID NO:2 and SEQ ID NO:4.

In one embodiment, the nucleic acid molecule is a DNA molecule or an RNA molecule.

In one embodiment, the nucleic acid molecule comprises a nucleotide sequence of a) a nucleotide sequence having at least about 90% identity over an entire length of a nucleotide sequence selected from the group consisting of SEQ ID NO:1 and SEQ ID NO:3, b) an immunogenic fragment of a nucleotide sequence having at least about 90% identity over at least 60% of the nucleotide sequence selected from the group consisting of SEQ ID NO:1 and SEQ ID NO:3, c) a nucleotide sequence selected from the group consisting of SEQ ID NO:1 and SEQ ID NO:3, or d) an immunogenic fragment of a nucleotide sequence selected from the group consisting of SEQ ID NO:1 and SEQ ID NO:3.

In one embodiment, the encoding nucleotide sequence is operably linked to at least one regulatory sequence selected from the group consisting of a start codon, a nucleotide sequence encoding an IgE leader sequence and a stop codon.

In one embodiment, the nucleic acid molecule encodes a peptide comprising an amino acid sequence of a) an amino acid sequence having at least about 90% identity over an entire length of the amino acid sequence selected from the group consisting of SEQ ID NO:2 and SEQ ID NO:4, b) an immunogenic fragment comprising at least about 90% identity over at least 60% of the amino acid sequence selected from the group consisting of SEQ ID NO:2 and SEQ ID NO:4, c) the amino acid sequence selected from the group consisting of SEQ ID NO:2 and SEQ ID NO:4, or d) an immunogenic fragment comprising at least 60% of the amino acid sequence selected from the group consisting of SEQ ID NO:2 and SEQ ID NO:4.

In one embodiment, the nucleic acid molecule comprises a nucleotide sequence of a) a nucleotide sequence having at least about 90% identity over an entire length of a nucleotide sequence selected from the group consisting of SEQ ID NO:1 and SEQ ID NO:3, b) an immunogenic fragment of a nucleotide sequence having at least about 90% identity over at least 60% of the nucleotide sequence selected from the group consisting of SEQ ID NO:1 and SEQ ID NO:3, c) a nucleotide sequence selected from the group consisting of SEQ ID NO:1 and SEQ ID NO:3, or d) an immunogenic fragment of a nucleotide sequence selected from the group consisting of SEQ ID NO:1 and SEQ ID NO:3.

In one embodiment, the nucleic acid molecule is an expression vector.

In one embodiment, the nucleic acid molecule is a viral particle.

In one embodiment, the immunogenic composition comprises a pharmaceutically acceptable excipient.

In one embodiment, the immunogenic composition comprises an adjuvant.

In one embodiment, the nucleic acid molecule is selected from the group consisting of a DNA molecule and an RNA molecule.

In one embodiment, the nucleotide sequence is operably linked to at least one of a start codon, a nucleotide sequence encoding an IgE leader sequence and a stop codon.

In one embodiment, the invention relates to a method of treating or preventing a tumor associated pathology in subject in need thereof, the method comprising administering to the subject an immunogenic composition comprising a nucleic acid molecule, wherein the nucleic acid molecule encodes a peptide comprising an amino acid sequence of a) an amino acid sequence having at least about 90% identity over an entire length of the amino acid sequence selected from the group consisting of SEQ ID NO:2 and SEQ ID NO:4, b) an immunogenic fragment comprising at least about 90% identity over at least 60% of the amino acid sequence selected from the group consisting of SEQ ID NO:2 and SEQ ID NO:4, c) the amino acid sequence selected from the group consisting of SEQ ID NO:2 and SEQ ID NO:4, or d) an immunogenic fragment comprising at least 60% of the amino acid sequence selected from the group consisting of SEQ ID NO:2 and SEQ ID NO:4.

In one embodiment, the method of administering includes at least one of electroporation and injection.

In one embodiment, a tumor associated pathology is at least one of tumor growth, tumor metastasis, and angiogenesis.

In one embodiment, the subject has been diagnosed with cancer.

In one embodiment, the cancer is melanoma.

In one embodiment, the method further comprises administering an immunogenic composition comprising one or more cancer antigens to the subject.

In one embodiment, the subject is at high risk of developing cancer.

In one embodiment, the cancer is melanoma.

In one embodiment, the method further comprises administering an immunogenic composition comprising one or more skin cancer antigens to the subject.

DETAILED DESCRIPTION

In one aspect, the present invention provides an immunogenic composition targeting CSPG4 antigen. Further aspects of the present invention are treatments and/or preventions of cancer growth or metastasis using the disclosed immunogenic composition alone or in combination with additional cancer vaccines or therapeutics.

The sequence encoding the CSPG4 antigen of the invention is genetically diverged from the sequence encoding the native CSPG4 protein, and thus, the antigen of the invention is unique. The immunogenic composition of the present invention can be widely applicable to breaking tolerance to the native antigen, and reducing or preventing tumor growth or metastasis because of the unique sequences of the encoded antigen. These unique sequences allow the immunogenic composition to be protective against multiple types of cancer.

The immunogenic composition can be used to protect against and treat any number of cancers. The immunogenic composition can elicit both humoral and cellular immune responses that target the antigen. The immunogenic composition can elicit neutralizing antibodies and immunoglobulin G (IgG) antibodies that are reactive with the antigen. The immunogenic composition can also elicit a $CD8^+$ T cell response that is reactive to the antigen and produce one or more of interferon-gamma (IFN-γ) and tumor necrosis factor alpha (TNF-α). In one embodiment, the immunogenic composition can also elicit a $CD4^+$ T cell response that is reactive to the antigen and produce one or more of IFN-γ and TNF-α.

In one embodiment, the invention includes a nucleic acid vaccine against CSPG4. In one embodiment, the vaccine comprise a plasmid encoding a consensus CSPG4 antigen. In one embodiment, the consensus CSPG4 antigen further comprise mutations that disrupt the oncogenic features of native T antigens. As a vaccine candidate, an enhanced DNA (DNA)-based platform provides many advantages in genetic optimization and delivery techniques. As such, each CSPG4 antigen can be genetically-optimized, subcloned into modified mammalian expression vectors, and then delivered using in vivo electroporation (EP).

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the immunogenic composition described herein to enhance the immunogenicity of the antigen.

"Antibody" as used herein means an antibody of classes IgG, IgM, IgA, IgD or IgE, or fragments, fragments or derivatives thereof, including Fab, $F(ab')_2$, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes, serotypes, or strains of a particular antigen. Synthetic antigens, such as fusion proteins, may be manipulated to generate consensus sequences (or consensus antigens).

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, the term "expressible form" refers to gene constructs that contain the necessary regulatory elements operably linked to a coding sequence that encodes a target protein or an immunomodulating protein, such that when present in the cell of the individual, the coding sequence will be expressed.

"Fragment" as used herein means a nucleotide sequence or a portion thereof that encodes a polypeptide capable of eliciting an immune response in a mammal. The fragments can be DNA fragments selected from at least one of the various nucleotide sequences that encode protein fragments set forth below.

"Fragment" or "immunogenic fragment" with respect to polypeptide sequences means a polypeptide capable of eliciting an immune response in a mammal that cross reacts with a full length endogenous antigen. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a tumor microenvironment protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" as used herein can mean a mammal that is capable of being administered the immunogenic compositions described herein. The mammal can be, for example, a human, chimpanzee, dog, cat, horse, cow, mouse, or rat.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleotide sequence and a second nucleotide sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating," as used herein can mean protecting of a subject from a disease through means of preventing, suppressing, repressing, or completely eliminating the disease. In one embodiment, preventing the disease involves administering an immunogenic composition of the present invention to a subject prior to onset of the disease. In one embodiment, preventing the disease involves administering an immunogenic composition of the present invention to a subject following a treatment so as to prevent reoccurrence or further progression of the disease. Suppressing the disease involves administering an immunogenic composition of the present invention to a subject after induction of the disease but before its clinical appearance. Repressing the disease involves administering an immunogenic composition of the present invention to a subject after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleotide sequence that is substantially identical over the full length of the full gene sequence or a fragment thereof. The nucleotide sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

DESCRIPTION

The invention provides an optimized consensus sequence encoding a CSPG4 antigen. In one embodiment, the CSPG4 antigen encoded by the optimized consensus sequence is capable of eliciting an immune response in a mammal. In one embodiment, the CSPG4 antigen encoded by the optimized consensus sequence can comprise an epitope(s) that makes it particularly effective as an immunogen against which an immune response can be induced.

The optimized consensus sequence can be a consensus sequence derived from two or more native CSPG4 proteins. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The CSPG4 antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The antigen encoded by the optimized consensus sequence can be designed to elicit stronger cellular and/or humoral immune responses than a corresponding native antigen. The antigen encoded by the optimized consensus sequence can be designed to break tolerance and synergize with anti-cancer immune therapy.

In one embodiment, an optimized consensus CSPG4 is designed to break tolerance to native CSPG4. In one embodiment, an optimized consensus CSPG4 encoding sequence is as set forth in SEQ ID NO:1 or SEQ ID NO:3. In one embodiment, an optimized consensus CSPG4 encoded antigen has an amino acid sequence as set forth in SEQ ID NO:2 or SEQ ID NO:4.

In one embodiment, an optimized consensus encoded CSPG4 antigen is operably linked to one or more regulatory elements. In one embodiment, a regulatory element is a leader sequence. In one embodiment, the optimized consensus DNA sequence operably linked to an IgE leader encoding sequence is set forth in SEQ ID NO:3. In one embodiment, the optimized consensus-encoded CSPG4 antigen operably linked to an IgE leader sequence is as set forth in SEQ ID NO:4.

In one embodiment, a regulatory element is a start codon. Therefore, in one embodiment, the invention relates to a nucleic acid sequence as set forth in SEQ ID NO:1 or SEQ ID NO:3, or a fragment or homolog thereof, operably linked to a nucleotide sequence comprising a start codon at the 5' terminus. In one embodiment, the invention relates to an amino acid sequence as set forth in SEQ ID NO:2 or SEQ ID NO:4 or a fragment or homolog thereof, operably linked to an amino acid encoded by a start codon (e.g., a Methionine) at the N-terminus.

In one embodiment, a regulatory element is at least one stop codon. Therefore, in one embodiment, the invention relates to a nucleic acid sequence as set forth in SEQ ID NO:1 or SEQ ID NO:3 or a fragment or homolog thereof, operably linked to a nucleotide sequence comprising at least one stop codon at the 3' terminus. In one embodiment, the nucleotide sequence is operably linked to two stop codons to increase the efficiency of translational termination.

In one embodiment, the optimized consensus sequence encoding a CSPG4 antigen can encode a peptide having the amino acid sequence set forth in SEQ ID NO:2 or SEQ ID NO:4. In one embodiment, the optimized consensus sequence can have the nucleotide sequence set forth in SEQ ID NO:1 or SEQ ID NO:3. In some embodiments, the sequence can be the nucleotide sequence having at least about 96%, 97%, 98%, 99% identity over an entire length of the nucleotide sequence set forth in SEQ ID NO:1 or SEQ ID NO:3. In other embodiments, sequence can be the nucleotide sequence that encodes the amino acid sequence having at least about 96%, 97%, 98%, 99%, or 100% identity over an entire length of the amino acid sequence set forth in SEQ ID NO:2 or SEQ ID NO:4. In some embodiments, the optimized consensus CSPG4 antigen can be encoded by an RNA that is a transcript from a DNA sequence having at least about 96%, 97%, 98%, 99% or 100% identity over an entire length of the nucleic acid sequence set forth in the SEQ ID NO:1 or SEQ ID NO:3. In some embodiments, the optimized consensus CSPG4 antigen can be encoded by an RNA that encodes an amino acid sequence having at least about 96%, 97%, 98%, 99% or 100% identity over an entire length of the amino acid sequence set forth in SEQ ID NO:2 or SEQ ID NO:4.

The optimized consensus-encoded CSPG4 antigen can be a peptide having the amino acid sequence set forth in SEQ ID NO:2 or SEQ ID NO:4. In some embodiments, the antigen can have an amino acid sequence having at least about 96%, 97%, 98%, 99%, or 100% identity over an entire length of the amino acid sequence set forth in SEQ ID NO:2 or SEQ ID NO:4.

Immunogenic fragments of SEQ ID NO:2 or SEQ ID NO:4 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO:2 or SEQ ID NO:4. In some embodiments, immunogenic fragments include a leader sequence, such as for example an immunoglobulin leader, such as the IgE leader. In some embodiments, immunogenic fragments are free of a leader sequence.

In one embodiment, the nucleic acid sequence comprises an RNA sequence encoding a consensus CSPG4 immunogen sequence described herein. For example, nucleic acids may comprise an RNA sequence encoding one or more of SEQ ID NO:2 or SEQ ID NO:4, a variant thereof, a fragment thereof or any combination thereof.

Immunogenic fragments of proteins with amino acid sequences homologous to immunogenic fragments of SEQ ID NO:2 or SEQ ID NO:4 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2 or SEQ ID NO:4. Some embodiments relate to immunogenic fragments that have 90% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

Some embodiments relate to immunogenic fragments of SEQ ID NO:1 or SEQ ID NO: 3. Immunogenic fragments can be at least 60%, at least 65%, at least 70%, at least 75%, at least 80%, at least 85%, at least 90%, at least 95%, at least 96%, at least 97%, at least 98% or at least 99% of the full length of SEQ ID NO:1 or SEQ ID NO:3. Immunogenic fragments can be at least 96%, at least 97% at least 98% or at least 99% homologous to fragments of SEQ ID NO:1 or SEQ ID NO:3. In some embodiments, immunogenic fragments include sequences that encode a leader sequence, such as for example an immunoglobulin leader, such as the IgE leader. In some embodiments, fragments are free of coding sequences that encode a leader sequence.

Immunogenic Composition

Provided herein are immunogenic compositions, such as vaccines, comprising an optimized consensus sequence, an optimized consensus-encoded antigen, a fragment thereof, a variant thereof, or a combination thereof. The immunogenic composition can be used to reduce tumor growth or metastasis or protect against tumor development, thereby treating, preventing, and/or protecting against cancer based pathologies. The immunogenic composition can significantly induce an immune response of a subject administered with the immunogenic composition.

In one embodiment, the immunogenic composition can significantly induce an immune response of a subject administered with the immunogenic composition, thereby protecting against and treating cancer based pathologies in the subject.

The immunogenic composition can be a DNA vaccine, an RNA vaccine, a peptide vaccine, or a combination vaccine. The vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized consensus nucleotide sequence and the encoded antigen.

In one embodiment, immunogenic composition of the invention can be used to elicit protective anti-tumor immunity against, and prevent occurrence or recurrence of, e.g., melanoma or other cancers characterized by tumor cells bearing CSPG4, e.g., melanoma cells.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose.

In one embodiment, the compositions and methods described herein are useful for treatment of cancer and tumor cells, i.e., both malignant and benign tumors, so long as the cells to be treated express CSPG4. Thus, in various embodiments of the methods and compositions described herein, the cancer can include, without limitation, prostate cancer, lung carcinomas, non-small cell lung carcinoma, malignant sarcoma, breast cancer, pancreatic cancer, melanoma, blood cancers (e.g., leukemia, lymphoma, myeloma), esophageal squamous cell carcinomas, bladder cancer, colorectal cancer, esophagus, gastric cancer, hepatocarcinoma, head and neck cancer, brain cancer, anal cancer, synovial carcinoma, testicular cancer, liver cancer, cervical cancer, recurrent respiratory papillomatosis, skin cancer and stomach cancer.

In one embodiment, the immunogenic composition can be a vaccine. The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510, 245; 4,797,368; 4,722,848; 4,790,987; 4,920,209; 5,017, 487; 5,077,044; 5,110,587; 5,112,749; 5,174,993; 5,223, 424; 5,225,336; 5,240,703; 5,242,829; 5,294,441; 5,294, 548; 5,310,668; 5,387,744; 5,389,368; 5,424,065; 5,451, 499; 5,453,364; 5,462,734; 5,470,734; 5,474,935; 5,482, 713; 5,591,439; 5,643,579; 5,650,309; 5,698,202; 5,955, 088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose.

In one embodiment, an immunogenic composition of the invention comprises a CSPG4 antigen and one or more additional cancer antigens.

Combinational Immunogenic Compositions for Treating Particular Cancers

The immunogenic composition can be in the form of various combinations of the antigen as described above with one or more cancer antigens to treat particular cancers or tumors. Depending upon the combination of one or more cancer antigens, various cancers or other tumor types may be targeted with the immunogenic composition. These cancers can include, but are not limited to ovarian cancer, prostate cancer, breast cancer, colon cancer, pancreatic cancer, urinary bladder cancer, kidney cancer, lung cancer, liver cancer, stomach cancer, skin, and testicular cancer.

Cancer Antigens

The immunogenic composition can comprise one or more cancer antigens such as WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGS5, SART3, STn, Carbonic anhydrase IX, PAXS, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen 1 to treat or prevent a tumor associated pathology. The immunogenic composition can further combine one or more cancer antigens WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGS5, SART3, STn, Carbonic anhydrase IX, PAXS, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen with an optimized consensus encoded CSPG4 antigen for treating or preventing a tumor associated pathology. Other combinations of cancer antigens may also be applied for treating or preventing a tumor associated pathology.

Ovarian Cancer Antigens

The immunogenic composition can comprise one or more cancer antigens such as CA-125, Beta human chorionic gonadotropin (beta-hCG), Urinary gonadotropin fragment, Alpha-fetoprotein (AFP), Inhibin, Carcinoembryonic antigen (CEA), Squamous cell carcinoma (SCC) antigen, Mullerian inhibiting substance (MIS), Topoisomerase II, Carbohydrate antigen 19-9, Cancer antigen 27-29, Human telomerase reverse transcriptase (hTERT) and Ferritin to treat or prevent ovarian cancer. The immunogenic composition can further combine one or more cancer antigens CA-125, Beta human chorionic gonadotropin (beta-hCG), Urinary gonadotropin fragment, Alpha-fetoprotein (AFP), Inhibin, Carcinoembryonic antigen (CEA), Squamous cell carcinoma (SCC) antigen, Mullerian inhibiting substance (MIS), Topoisomerase II, Carbohydrate antigen 19-9, Cancer antigen 27-29, Human telomerase reverse transcriptase (hTERT) and Ferritin with a CSPG4 antigen, for treating or preventing ovarian cancer. Other combinations of cancer antigens may also be applied for treating or preventing ovarian cancer.

Prostate Cancer Antigens

The immunogenic composition can comprise one or more cancer antigens such as PSA, PSMA, or STEAP to treat or prevent prostate cancer. The immunogenic composition can further combine one or more cancer antigens PSA, PSMA, or STEAP with a CSPG4 antigen for treating or preventing prostate cancer. Other combinations of cancer antigens may also be applied for treating or preventing prostate cancer. Exemplary PSA, PSMA, and STEP antigens, as well as nucleic acid molecules encoding such antigens, are disclosed in PCT application no. PCT/US11/60592 and corresponding U.S. Pat. No. 8,927,692, which are incorporated herein by reference.

Breast Cancer Antigens

The immunogenic composition can comprise one or more cancer antigens such as HER2, MUC-1, CEA, MAGE-3 and NY-ESO-1 to treat or prevent breast cancer. The immunogenic composition can further combine one or more cancer antigens HER2, MUC-1, CEA, MAGE-3 and NY-ESO-1 with a CSPG4 antigen for treating or preventing breast cancer. Other combinations of cancer antigens may also be applied for treating or preventing breast cancer.

Lung Cancer Antigens

The immunogenic composition can comprise one or more cancer antigens such as TERT, CD22, MAGE-3 and NY-ESO-1 to treat or prevent lung cancer (see FIG. 13). The immunogenic composition can further combine one or more cancer antigens TERT, CD22, MAGE-3 and NY-ESO-1 with a FAP antigen for treating or preventing lung cancer. Other combinations of cancer antigens may also be applied for treating or preventing lung cancer.

Pancreatic Cancer Antigens

The immunogenic composition can comprise one or more cancer antigens such as MUC-1, CEA, HER2, Mesothelin, Survivin, and VEGFR2 to treat or prevent pancreatic cancer. The immunogenic composition can further combine one or more cancer antigens MUC-1, CEA, HER2, Mesothelin, Survivin, and VEGFR2 with a CSPG4 antigen for treating or preventing pancreatic cancer. Other combinations of cancer antigens may also be applied for treating or preventing pancreatic cancer.

Lung Cancer Antigens

The immunogenic composition can comprise one or more cancer antigens such as TERT, CD22, MAGE-3 and NY-ESO-1 to treat or prevent lung cancer. The immunogenic composition can further combine one or more cancer antigens TERT, CD22, MAGE-3 and NY-ESO-1 with a CSPG4 antigen for treating or preventing lung cancer. Other combinations of cancer antigens may also be applied for treating or preventing lung cancer.

Melanoma Antigens

The immunogenic composition can comprise one or more cancer antigens such as tyrosinase, PRAME, or GP100-Trp2 to treat or prevent melanoma. The immunogenic composition can further combine one or more cancer antigen tyrosinase, PRAME, or GP100-Trp2 with a CSPG4 antigen for treating or preventing melanoma. Other combinations of cancer antigens may also be applied for treating or preventing melanoma.

Liver Cancer Antigens

The immunogenic composition can comprise one or more cancer antigens such as HBV core antigen, HBV surface antigen, HCVNS34A, HCVNS5A, HCV NS5B, or HCVNS4B to treat or prevent liver cancer. The immunogenic composition can further combine one or more cancer antigens HBV core antigen, HBV surface antigen, HCVNS34A, HCVNS5A, HCV NS5B, or HCVNS4B with a CSPG4 antigen for treating or preventing liver cancer. Other combinations of cancer antigens may also be applied for treating or preventing liver cancer.

Glioblastoma Antigens

The immunogenic composition can comprise CMV to treat or prevent glioblastoma. The immunogenic composition can further combine CMV with a CSPG4 antigen for treating or preventing glioblastoma. Other combinations of cancer antigens may also be applied for treating or preventing glioblastoma.

Blood Cancer Antigens

The immunogenic composition can comprise one or more cancer antigens such as PRAME, WT-1, hTERT to treat or prevent blood cancers such as leukemia, lymphoma and myeloma. The immunogenic composition can further combine one or more cancer antigens PRAME, WT-1, hTERT with a CSPG4 antigen for treating or preventing blood cancers such as leukemia, lymphoma and myeloma. Other combinations of cancer antigens may also be applied for treating or preventing blood cancers such as leukemia, lymphoma and myeloma cancer.

Immune Response

The immunogenic composition can induce an immune response in the subject administered the composition. The induced immune response can be specific for a native antigen. The induced immune response can be reactive with a native antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for a native antigen. The induced humoral immune response can be reactive with the native antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized CSPG4 antigen.

The humoral immune response induced by the immunogenic composition can include an increased level of neutralizing antibodies associated with the subject administered the immunogenic composition as compared to a subject not administered the immunogenic composition. The neutralizing antibodies can be specific for a native antigen related to the optimized consensus-encoded antigen. The neutralizing antibodies can be reactive with the native antigen genetically related to the optimized consensus antigen. The neutralizing antibodies can provide protection against and/or treatment of tumor growth, metastasis or tumor associated pathologies in the subject administered the immunogenic composition.

The humoral immune response induced by the immunogenic composition can include an increased level of IgG antibodies associated with the subject administered the immunogenic composition as compared to a subject not administered the immunogenic composition. These IgG antibodies can be specific for the native antigen genetically related to the optimized consensus antigen. These IgG antibodies can be reactive with the native antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized CSPG4 antigen.

The immunogenic composition can induce a cellular immune response in the subject administered the immunogenic composition. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a CD8$^+$ T cell response. The elicited CD8$^+$ T cell response can be reactive with the native antigen genetically related to the optimized consensus antigen. The elicited CD8$^+$ T cell response can be polyfunctional. The induced cellular immune response can include eliciting a CD8$^+$ T cell response, in which the CD8$^+$ T cells produce interferon-gamma (IFN-γ), tumor necrosis factor alpha (TNF-α), interleukin-2 (IL-2), or a combination of IFN-γ and TNF-α.

The induced cellular immune response can include an increased CD8$^+$ T cell response associated with the subject administered the immunogenic composition as compared to the subject not administered the immunogenic composition. The CD8$^+$ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8$^+$ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized CSPG4 antigen.

The induced cellular immune response can include an increased frequency of CD107a/IFNγ/T-bet triple-positive CD8 T cells that are reactive against the native antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized CSPG4 antigen.

The induced cellular immune response can include an increased frequency of CD107a/IFNγ double-positive CD8 T cells that are reactive against the native antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized CSPG4 antigen.

The cellular immune response induced by the immunogenic composition can include eliciting a CD4$^+$ T cell response. The elicited CD4$^+$ T cell response can be reactive with the native antigen genetically related to the optimized consensus antigen. The elicited CD4$^+$ T cell response can be polyfunctional. The induced cellular immune response can include eliciting a CD4$^+$ T cell response, in which the CD4$^+$ T cells produce IFN-γ, TNF-α, IL-2, or a combination of IFN-γ and TNF-α.

The induced cellular immune response can include an increased frequency of CD4$^+$ T cells that produce IFN-γ. The frequency of CD4$^+$IFN-γ$^+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized CSPG4 antigen.

The induced cellular immune response can include an increased frequency of CD4+ T cells that produce TNF-α. The frequency of CD4+TNF-α+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized CSPG4 antigen.

The induced cellular immune response can include an increased frequency of CD4+ T cells that produce both IFN-γ and TNF-α. The frequency of CD4+IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized CSPG4 antigen.

The immunogenic composition of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic composition can further induce an immune response when administered to different tissues such as the muscle or skin. The immunogenic composition can further induce an immune response when administered via electroporation, or injection, or subcutaneously, or intramuscularly.

Fragments

In one embodiment, the immunogenic fragment is an immunogenic fragment of a full length antigen of the invention. As used herein, an immunogenic fragment is a fragment of a full length nucleic acid or amino acid sequence that can induce an immune response significantly similar to that of the full length sequence. In one embodiment, an immunogenic fragment comprises an immunogenic epitope of a full length sequence. In one embodiment, the immunogenic fragment induces an immune response at least about 0.7-fold, at least about 0.8-fold, at least about 0.9-fold, at least about 1.0-fold, at least about 1.1-fold, at least about 1.2-fold, at least about 1.3-fold, at least about 1.4-fold, at least about 1.5-fold, at least about 2.0-fold or greater than 2.0-fold as compared to the full length sequence.

The immunogenic fragment can induce a humoral immune response in the subject administered the immunogenic fragment. The humoral immune response can be induced in the subject administered the immunogenic fragment by about 1.5-fold to about 16-fold, about 2-fold to about 12-fold, or about 3-fold to about 10-fold. The humoral immune response can be induced in the subject administered the immunogenic fragment by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered immunogenic fragment.

The humoral immune response induced by the immunogenic fragment can include an increased level of IgG antibodies associated with the subject administered the immunogenic fragment as compared to a subject not administered the immunogenic fragment. The level of IgG antibody associated with the subject administered the immunogenic fragment can be increased by about 1.5-fold to about 16-fold, about 2-fold to about 12-fold, or about 3-fold to about 10-fold as compared to the subject not administered the immunogenic fragment. The level of IgG antibody associated with the subject administered the immunogenic fragment can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic fragment.

The immunogenic fragment can induce a cellular immune response in the subject administered the immunogenic fragment. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a CD8+ T cell response. The elicited CD8+ T cell response can be reactive with the native antigen genetically related to the optimized consensus antigen. The elicited CD8+ T cell response can be polyfunctional. The induced cellular immune response can include eliciting a CD8+ T cell response, in which the CD8+ T cells produce interferon-gamma (IFN-γ), tumor necrosis factor alpha (TNF-α), interleukin-2 (IL-2), or a combination of IFN-γ and TNF-α.

The induced cellular immune response can include an increased CD8+ T cell response associated with the subject administered the immunogenic fragment as compared to the subject not administered the immunogenic fragment. The CD8+ T cell response associated with the subject administered the immunogenic fragment can be increased by about 2-fold to about 30-fold, about 3-fold to about 25-fold, or about 4-fold to about 20-fold as compared to the subject not administered the immunogenic fragment. The CD8+ T cell response associated with the subject administered the immunogenic fragment can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic fragment.

The induced cellular immune response can include an increased frequency of CD107a/IFNγ/T-bet triple-positive CD8 T cells that are reactive against the native antigen. The frequency of CD107a/IFNγ/T-bet triple-positive CD8 T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic fragment.

The induced cellular immune response can include an increased frequency of CD107a/IFNγ double-positive CD8 T cells that are reactive against the native antigen. The frequency of CD107a/IFNγ double-positive CD8 T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic.

The cellular immune response induced by the immunogenic fragment can include eliciting a $CD4^+$ T cell response. The elicited $CD4^+$ T cell response can be reactive with the native antigen genetically related to the optimized consensus antigen. The elicited $CD4^+$ T cell response can be polyfunctional. The induced cellular immune response can include eliciting a $CD4^+$ T cell response, in which the $CD4^+$ T cells produce IFN-γ, TNF-α, IL-2, or a combination of IFN-γ and TNF-α.

The induced cellular immune response can include an increased frequency of $CD4^+$ T cells that produce IFN-γ. The frequency of $CD4^+IFN$-γ$^+$ T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic fragment.

The induced cellular immune response can include an increased frequency of $CD4^+$ T cells that produce TNF-α. The frequency of $CD4^+TNF$-α$^+$ T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic fragment.

The induced cellular immune response can include an increased frequency of $CD4^+$ T cells that produce both IFN-γ and TNF-α. The frequency of $CD4^+IFN$-γ$^+TNF$-α$^+$ associated with the subject administered the immunogenic fragment can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic fragment.

The immunogenic fragment of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic fragment can further induce an immune response when administered to different tissues such as the muscle or skin. The immunogenic fragment can further induce an immune response when administered via electroporation, or injection, or subcutaneously, or intramuscularly.

Vector

The nucleotide construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

Plasmid

The one or more vectors can be a plasmid. The plasmid may be useful for transfecting cells with the recombinant nucleic acid construct. The plasmid may be useful for introducing the recombinant nucleic acid construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO:1 or SEQ ID NO:3, or a variant thereof or a fragment thereof. In another embodiment, the nucleotide sequence comprises an RNA sequence transcribed by a DNA sequence encoding a polypeptide sequence at least 90% homologous to one of SEQ ID NO:2 or SEQ ID NO:4 or a variant thereof or a fragment thereof. Accordingly, in one embodiment, the invention provides an RNA molecule encoding one or more of the CSPG4 antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid immunogenic composition, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleotide sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleotide sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Method of Preparing the Vector

Provided herein is a method for preparing the one or more vectors in which the recombinant nucleic acid construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described elsewhere herein in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Multiple Vectors

The immunogenic composition may comprise a plurality of copies of a single nucleic acid molecule such a single plasmid, or a plurality of copies of two or more different nucleic acid molecules such as two or more different plasmids. For example an immunogenic composition may comprise plurality of two, three, four, five, six, seven, eight, nine or ten or more different nucleic acid molecules. Such compositions may comprise plurality of two, three, four, five, six, or more different plasmids.

Immunogenic compositions may comprise nucleic acid molecules, such as plasmids, that collectively contain coding sequence for a CSPG4 antigen. Immunogenic compositions may comprise nucleic acid molecules, such as plasmids, that collectively contain coding sequence for multiple antigens. In one embodiment, the antigens are a CSPG4 antigen and one or more additional cancer antigen. Immunogenic compositions may comprise nucleic acid molecules, such as plasmids, that collectively contain coding sequence for one or more antigen and one or more cancer antigen.

Cancer Antigens

The immunogenic composition can comprise one or more cancer antigens such as WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML- IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGS5, SART3, STn, Carbonic anhydrase IX, PAXS, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen 1 to treat or prevent a tumor associated pathology. The immunogenic composition can further combine one or more cancer antigens WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGS5, SART3, STn, Carbonic anhydrase IX, PAXS, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen with an optimized consensus encoded CSPG4 antigen for treating or preventing a tumor associated pathology. Other combinations of cancer antigens may also be applied for treating or preventing a tumor associated pathology.

Methods

Provided herein are methods of treating, protecting against, and/or preventing a CSPG4 associated disease in a subject in need thereof by administering one or more immunogenic composition described herein to the subject. Administration of the immunogenic composition to the subject can induce or elicit an immune response in the subject.

Provided herein is a method for delivering the immunogenic composition for providing genetic constructs and proteins of the consensus antigen which comprise epitopes that make them particular effective against CSPG4. The method of delivering the immunogenic composition or vaccination may be provided to induce a therapeutic and prophylactic immune response. The vaccination process may generate in the mammal an immune response against CSPG4. The immunogenic composition may be delivered to an individual to modulate the activity of the mammal's immune system and enhance the immune response. The delivery of the immunogenic composition may be the transfection of the consensus antigen as a nucleic acid molecule that is expressed in the cell and delivered to the surface of the cell upon which the immune system recognized and induces a cellular, humoral, or cellular and humoral response. The delivery of the immunogenic composition may be used to induce or elicit and immune response in mammals against CSPG4 by administering to the mammals the immunogenic composition as discussed above.

Upon delivery of the immunogenic composition and plasmid into the cells of the mammal, the transfected cells will express and secrete consensus antigens for each of the plasmids injected from the immunogenic composition. These proteins will be recognized as foreign by the immune system and antibodies will be made against them. These antibodies will be maintained by the immune system and allow for an effective response.

The immunogenic composition may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced cellular immune response can include a $CD8^+$ T cell response, which is induced by about 2-fold to about 30-fold, about 3-fold to about 25-fold, or about 4-fold to about 20-fold.

The immunogenic composition dose can be between 1 μg to 10 mg active component/kg body weight/time, and can be 20 μg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The immunogenic composition can be administered prophylactically or therapeutically. In prophylactic administration, the immunogenic compositions can be administered in an amount sufficient to induce an immune response. In therapeutic applications, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the subject, and the judgment of the prescribing physician.

The immunogenic composition can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The nucleic acid of the immunogenic composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunogenic composition can be delivered via a variety of routes. Typical delivery routes include parenteral administration, e.g., intradermal, intramuscular or subcutaneous delivery. Other routes include oral administration, intranasal, and intravaginal routes. For the nucleic acid of the immunogenic composition in particular, the immunogenic composition can be delivered to the interstitial spaces of tissues of an individual (Feigner et al., U.S. Pat. Nos. 5,580,859 and 5,703,055, the contents of all of which are incorporated herein by reference in their entirety). The immunogenic composition can also be administered to muscle, or can be administered via intradermal or subcutaneous injections, or transdermally, such as by iontophoresis. Epidermal administration of the immunogenic composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunogenic composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunogenic composition.

The immunogenic composition can be a liquid preparation such as a suspension, syrup or elixir. The immunogenic composition can also be a preparation for parenteral, subcutaneous, intradermal, intramuscular or intravenous administration (e.g., injectable administration), such as a sterile suspension or emulsion.

The immunogenic composition can be incorporated into liposomes, microspheres or other polymer matrices (Feigner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

Method of Cancer Treatment with the Vaccine

The vaccine can be used to generate or elicit an immune response in a mammal that is reactive or directed to a cancer or tumor (e.g., melanoma) of the mammal or subject in need thereof. The elicited immune response can prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8+ (CTL) to attack and kill tumor cells; (3) increase T helper cell responses; (4) and increase inflammatory responses via IFN-γ and TFN-α or preferably all of the aforementioned.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the administered vaccine can increase tumor free survival, reduce tumor mass, increase tumor survival, or a combination thereof in the subject. The administered vaccine can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject. The administered vaccine can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the cancerous or tumor tissue in the subject, thereby reducing vascularization of the cancerous or tumor tissue in the subject.

The administered vaccine can increase tumor survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject. In some embodiments, the vaccine can be administered to the periphery (as described in more detail below) to establish an antigen-specific immune response targeting the cancerous or tumor cells or tissue to clear or eliminate the cancer or tumor expressing CSPG4 without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The vaccine dose can be between 1 µg to 10 mg active component/kg body weight/time and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

Combinational Therapies with Checkpoint Inhibitors

The present invention is also directed to a method of increasing an immune response in a mammal using the vaccine as described above in combination with one or more checkpoint inhibitor. In one embodiment, the vaccine as described above can comprise the CSPG4 antigen and a checkpoint inhibitor (e.g., an antibody to a checkpoint protein). "Checkpoint inhibitor" as used herein includes inhibitors or molecules that block immune checkpoints as commonly understood in the field of cancer immunotherapy. More commonly the checkpoint inhibitors are antibodies that block the immune checkpoint proteins. Immune checkpoint proteins include, but are not limited to, PD1, PDL1, PDL2, CTLA-4, LAG3, TIM3, B7-H3, BTLA, VISTA, CD40, CEACAM1, CD80, CD86, OX40, CD27, GITR, DNAM-1, TIGIT, TMIGD2 and DC-SIGN. Some examples of known checkpoint inhibitors include, but are not limited to, ipilimumab, pembrolizumab, nivolumab, pidilizumab, avelumab and others.

The combination can be in a single formulation or can be separate and administered in sequence (either CSPG4 antigen first and then checkpoint inhibitor, or checkpoint inhibitor first and then CSPG4 antigen). In some embodiments, the CSPG4 antigen can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the checkpoint inhibitor is administered to the subject. In other embodiments, the checkpoint inhibitor can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the CSPG4 antigen is administered to the subject.

The combination of the CSPG4 antigen and checkpoint inhibitor induces the immune system more efficiently than a vaccine comprising the CSPG4 antigen alone. This more efficient immune response provides increased efficacy in the treatment and/or prevention of a particular cancer.

In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

Combination Treatments

The immunogenic composition may be administered in combination with other proteins and/or genes encoding CCL20, α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, WIC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the immunogenic composition is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL02, IL-12 protein, IL-15 protein, IL-28 protein, CTACK protein, TECK protein, MEC protein or RANTES protein or functional fragments thereof.

The immunogenic composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The immunogenic composition may be administered by traditional syringes, needleless injection devices, "microprojectile bombardment gone guns", or other physical methods such as electroporation ("EP"), "hydrodynamic method", or ultrasound.

The plasmid of the immunogenic composition may be delivered to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

Electroporation

Administration of the immunogenic composition via electroporation may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, Pa.) or Elgen electroporator (Inovio Pharmaceuticals, Plymouth Meeting, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the immunogenic compositions of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the immunogenic compositions include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

Generation of Antigens In Vitro and Ex Vivo

In one embodiment, the optimized consensus CSPG4 antigen is generated in vitro or ex vivo. For example, in one embodiment, a nucleic acid encoding an optimized consensus CSPG4 antigen can be introduced and expressed in an in vitro or ex vivo cell.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Optimized Consensus CSPG4 Immunogenic Composition

Chondroitin sulfate proteoglycan 4 (CSPG4), a transmembrane glycoprotein with functional roles in tumor migration, invasion, angiogenesis, and metastasis, has emerged as a promising tumor antigen target due to its overexpression in several solid cancer types and limited expression in normal tissue. In this study, a synthetic consensus DNA vaccine targeting CSPG4 was designed. The immunogenicity and preclinical efficacy of the vaccine was assessed in a tumor-bearing mouse model of melanoma.

Methods

C57BL/6 mice (n=5 per group) were immunized with 25 µg of SynCon® CSPG4 or vector control. Four immunizations were administered, two weeks apart, with electroporation following each immunization. Cellular immune responses were measured by mouse IFN-γ ELISpot and flow cytometry. The breadth and magnitude of antigen-specific T-cell epitopes was further assessed by epitope mapping using consensus matched peptides.

Vaccine-induced anti-tumor immunity was assessed in C57BL/6 mice transplanted with $5 \times 10^4$ YUMM1.7 murine melanoma cells (n=10). One week following implantation, these mice were immunized with 25 µg of SynCon® CSPG4. At the same time, naïve mice (n=10) were challenged with $5 \times 10^4$ YUMM1.7 tumor cells as a control.

Results

SynCon® CSPG4 generated strong cellular immune responses in mice, as assessed by IFN-γELISpot and flow cytometry. An average of over 800 SFU/$10^6$ splenocytes were elicited in mice vaccinated with SynCon® CSPG4. The percentage of $CD8^+IFN-\gamma^+$ cells in mice immunized with SynCon® CSPG4 (0.552%) was significantly higher than that of the control mice (0.09%) ($p<0.0442$). Additionally, the SynCon® CSPG4-vaccinated mice showed a significant increase in the percentage of $CD8^+CD107a^+$ T cells, an indicator of cytotoxic potential, compared to control mice (1.07% vs. 0.034%, respectively ($p<0.01$)). Epitope mapping revealed that SynCon® CSPG4 could elicit broad T-cell immune responses. Notably, SynCon® CSPG4 generated cellular responses against three peptide sequences identical to native mouse CSPG4 sequences, suggesting SynCon® CSPG4 is capable of breaking tolerance. Importantly, SynCon® CSPG4 significantly slowed tumor growth and increased survival in the YUMM1.7 mouse model of melanoma.

The results presented herein demonstrate that a DNA-based, synthetic consensus CSPG4 immunogen induced robust anti-tumor immunity. DNA immunogens designed by SynCon® technology have the potential to break tolerance and induce anti-tumor immunity in cancer patients. Without wishing to be bound by any particular theory, the vaccine can be used alone or in combination with checkpoint inhibitors as a therapy against cancer.

Example 2: Sequences

| Type | Description |
| --- | --- |
| SEQ ID NO: 1   Nucleotide | Synthetic consensus CSPG4 |
| SEQ ID NO: 2   Amino acid | Synthetic consensus CSPG4 |
| SEQ ID NO: 3   Nucleotide | Synthetic consensus CSPG4 operably linked to IgE leader sequence |
| SEQ ID NO: 4   Amino acid | Synthetic consensus CSPG4 operably linked to IgE leader sequence |
| SEQ ID NO: 5   Nucleotide | Full plasmid sequence for pGX1416, comprising CSPG4 coding DNA sequence |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An immunological composition comprising a synthetic nucleic acid encoding a consensus Chondroitin sulfate proteoglycan 4 (CSPG4) antigen, wherein the consensus CSPG4 antigen comprises an amino acid sequence selected from the group consisting of SEQ ID NO:2, SEQ ID NO:4, an amino acid sequence that is 96% identical or greater to SEQ ID NO:2, and an amino acid sequence that is 96% identical or greater to SEQ ID NO:4.

2. The immunological composition of claim 1, wherein the synthetic nucleic acid comprises a nucleotide sequence selected from the group consisting of: SEQ ID NO:1, SEQ ID NO:3, a nucleotide sequence that is 90% identical or greater to SEQ ID NO:1, and a nucleotide sequence that is 90% identical or greater to SEQ ID NO: 3.

3. The immunological composition of claim 1, wherein the synthetic nucleic acid is selected from the group consisting of a DNA molecule and an RNA molecule.

4. The immunological composition of claim 1, wherein the synthetic nucleic acid is incorporated into one or more plasmids.

5. The immunological composition of claim 1, wherein the synthetic nucleic acid further comprises a nucleotide sequence encoding an adjuvant.

6. The immunological composition of claim 1, wherein the composition further comprises one or more nucleic acids encoding one or more additional cancer antigens.

7. The immunological composition of claim 1, wherein the composition further comprises one or more nucleic acids encoding one or more immune checkpoint inhibitors.

8. The immunological composition of claim 1, wherein the synthetic nucleic acid encoding the consensus CSPG4 antigen is operably linked to at least one regulatory sequence selected from the group consisting of a start codon, an IgE leader sequence and a stop codon.

9. The immunological composition of claim 1, wherein the nucleic acid is incorporated into an expression vector.

10. The immunological composition of claim 1, wherein the nucleic acid is incorporated into a viral particle.

11. The immunological composition of claim 1, further comprising a pharmaceutically acceptable excipient.

12. A method of treating a cancer that expresses CSPG4 in a subject in need thereof, the method comprising administering the immunological composition of claim 1 to the subject.

13. The method of claim 12, wherein the administering step comprises electroporation.

14. The method of claim 12, further comprising administering one or more nucleotide sequences encoding one or more immune checkpoint inhibitors.

15. The method of claim 12, wherein the method further comprises administering an immunogenic composition comprising one or more cancer antigen to the subject.

16. The method of claim 12, wherein the cancer is melanoma.

17. A method of inducing an immune response against Chondroitin sulfate proteoglycan 4 (CSPG4) in a subject in need thereof, the method comprising administering an immunogenic composition of claim 1 to the subject.

18. The method of claim 16, wherein the administering step comprises electroporation.

19. A nucleic acid molecule comprising one or more nucleotide sequences selected from the group consisting of: SEQ ID NO:1, SEQ ID NO:3, a nucleotide sequence that is 90% identical or greater to SEQ ID NO:1, and a nucleotide sequence that is 90% identical or greater to SEQ ID NO:3.

20. A protein comprising one or more amino acid sequences selected from the group consisting of: SEQ ID NO:2, SEQ ID NO:4, an amino acid sequence that is 96% identical or greater to SEQ ID NO:2, and an amino acid sequence that is 96% identical or greater to SEQ ID NO:4.

* * * * *

SEQUENCE LISTING

```
<160> NUMBER OF SEQ ID NOS: 5

<210> SEQ ID NO 1
<211> LENGTH: 6960
<212> TYPE: DNA
<213> ORGANISM: Artificial Sequence
<220> FEATURE:
<223> OTHER INFORMATION: Synthetic consensus CSPG4

<400> SEQUENCE: 1
cagtctggac ctcgaccccc tctgcccgcc cctgcactgg ccctggctct gaccctggca      60
atgctggcaa gagcctccgc cgcttctttc tttggcgaaa accacctgga ggtgcccgtc     120
gctacagcac tgactgacat cgatctgcag ctgcagttca gcacatccca gccagaggcc     180
```

-continued

```
ctgctgctgc tggcagcagg ccctgctgac catctgctgc tgcagctgta cagcggaaga      240
ctgcaggtca ggctggtgct gggacaggag gaactgcgac tgcagacacc agccgagact      300
ctgctgtctg atagtgtccc ccacaccgtg gtcctgacag tgtcagacag ctgggccacc      360
ctgtccgtcg atggactgct gaacgcatct gctccagtgc aggagcccc tctggaggtc       420
ccatacggac tgttcgtggg cgggacaggc tctctgggac tgccatatct gcggggact       480
agtcggcccc tgagaggatg cctgcacgct gcaaccctga atggccgctc cctgctgcga      540
ccactgacac ctgacgtgca tgagggctgt gccgaggaat tttctgctgg ggacgatgtg      600
gcactgggat tctccggacc acactctctg gcagcttttc ctgcctgggg cacccaggat      660
gaagggactc tggagttcac cctgaccaca aggtcccgcc aggctcccct ggcatttcag      720
gccgaggcc gccacggcga cttcatctac gtggatattt ttgagggca tctgcgggcc        780
gtggtcgaaa aggggcaggg aacagtgctg ctgcacaact ctgtgccagt cgcagacggc      840
cagccccatg aagtgagtgt ccacatcgac gctcatagac tggagatttc agtggatcag      900
taccctaccc ggacaagcaa tagaggggtg ctgtcctatc tggagccaag gggaagcctg      960
ctgctgggcg cctggacgc agaggcctcc agacacctgc aggaacatag gctgggcctg       1020
gctcccgaag caacaaacgc ctccctgctg gggtgcatgg aggatctgtc tgtgaatgga      1080
cagcgaagag gactgcgaga ggccctgctg actcgaaaca tggcagccgg atgtcggctg      1140
gaggaagagg aatatgagga agacgcttac ggcccttatg aggcattcag caccctggct      1200
cccgaagcat ggcctgccat ggaactgcct gagccatgcg tcccagagcc tggactgcct      1260
cccgtgttcg ccaacttcac ccagctgctg actatctctc cactggtggt cgcagagggc      1320
gggactgctt ggctggaatg gcgacacgtg cagcccaccc tggacctgag cgaggccgaa      1380
ctgcggaaat cccaggtgct gttttctgtc accaggggag ctcgccatgg cgagctggaa      1440
ctggatattc ccggagctca ggcaagaaaa atgttcacac tgctggacgt ggtcaaccga      1500
aaggcccggt ttgtgcacga tggcagtgaa gacacatcag atcagctggt gctggaggtg      1560
agtgtcactg ccagaggccc aatgccctca tgtctgaggc gcgggcagac ctacctgctg      1620
cctatccagg tcaacccagt gaatgaccca cccaggatca ttttcccaca cgggtccctg      1680
atggtcatcc tggagcatac acagaagcca ctgggacccg aggtgttcca ggcctatgac      1740
cccgatagcg cctgcgaggg cctgacttt cagctgctgg aaccccatc cggactgcca        1800
gtggaacgac gagatcagcc tggcgaacca gcaaccgagt tcagttgtcg cgagctggaa      1860
gccgggtcac tggtgtacgt ccacagagga ggcccagcac aggacctgac cttccgggtg      1920
agcgatggcc tgcaggctag tcctccagca actctgaaag tggtcgccgt gcggcctgct      1980
atccagatta gacatagcac cggactgagg ctggcacagg gctccgctgc acccatcctg      2040
cctgccaacc tgtctgtcga gaccaatgct gtgggccagg acgtgagtgt cctgttcagg      2100
gtgacaggag ccctgcagtt tggagagctg cagaagcagg gagcaggggg agtggaagga     2160
gcagagtggt gggctaccca ggcattccac cagcgagatg tcgagcaggg acgagtgcgg      2220
tacctgagca ccgaccccca gcatcgggca gaagatacag tggagaacct ggccctggag      2280
gtgcaggtcg acaggaaac actgagtaat ctgtcatttc ccgtcaccat tcagagggcc      2340
acagtgtgga tgctgcgcct ggagcctctg cacacccaga acacacagca ggaggcactg      2400
actaccgccc atctggaagc tactctggag gaagcaggac ctagccctcc caccttccac      2460
tatgaggtgg tccaggctcc acgcaagggc aatctgcagc tgcagggaac tagactgtct      2520
gacggacagg ggtttaccca ggacgatctg caggcaggac gagtgaccta cggagcaaca      2580
```

```
gccagagcca gtgaagccgt cgaggatacc ttccggttcc gggtgactgc tccaccccac   2640
ttctctcccc tgtatacttt tcctatccat attggcgggg acccagatgc acccgtgctg   2700
accaacgtcc tgctgtccgt gccagaagga ggcgagggcg tcctgagcgc agaccacctg   2760
ttcgtgaaat ccctgaattc cgcctcttac ctgtatgaag tgatggagcg accacgacat   2820
ggaaggctgg catggcgagg aacccaggac aagacaacta tggtgactag cttcaccaac   2880
gaggatctgt gcggggcag actggtgtac cagcacgacg attccgaaac cacagaggac   2940
gatatcccct tgtggctac tagacaggga gagggctctg ggacatggc atgggaggaa    3000 gtccgaggcg tgttccgggt cgctatccag cctgtcaatg atcacgcacc agtgcagaca   3060
attagccgcg tgtttcatgt cgcccgaggg ggaagaaggc tgctgactac cgacgatgtg   3120
gcattcagcg acgccgattc cggatttgcc gacgctcagc tggtgctgac caggaaagat   3180
ctgctgttcg gctccatcgt ggccgtcgac gaacctacca gaccaatcta caggttcaca   3240
caggaggatc tgcgcaagcg ccgagtgctg tttgtccact ccggagcaga ccgaggatgg   3300
attcagctgc aggtgtctga tggccagcat caggcaaccg ccctgctgga agtccaggcc   3360
tctgagccct atctgcgcgt ggctaacggg agctccctgg tggtccctca gggcgggcag   3420
ggaacaatcg acactgccgt gctgcacctg gacacaaatc tggatattcg gagcggagat   3480
gaggtccact accatgtgac tgctggacca cgatggggac agctgctgag agcaggacag   3540
ccagctaccg cattcagtca gcaggacctg ctggatggag ccatcctgta ttcacacaac   3600
ggcagtctgt cacccaggga cactctggcc ttcagcgtcg aggcaggacc tgtgcatacc   3660
gatgccacac tgcaggtgac cattgctctg aaggacccc tggcacctct gcacctggtc    3720
cagcataaga aaatctacgt gttccagggc gaagccgctg agattcggag agaccagctg   3780
gaagcagccc aggaggctgt gcctccagca gatatcgtgt tttcagtcaa aacccctccc   3840
agcgccggat acctggtcat ggtgagccac ggagccctgg ctgacgaacc cccagcctg    3900 gaccccgtgc agagcttctc ccaggaggca gtcgacgctg gacgagtgct gtatctgcat   3960
tcccggcctg aggcctggtc tgacgctttt agtctggatg tggcttctgg actgggcgca   4020
ccactggaag gggtgctggt cgagctggaa gtgctgcctg ctgcaatccc actggaggcc   4080
cagaatttct ccgtccctga aggaggctct cggaccctgg ctcctccact gctgagagtg   4140
accggcccat actttcccac actgcctgga ctgtccctgc aggtgctgga gccccctcag   4200
cacggcgccc tgcagagaga ggaaggaccc caggacagga cactgagcgc cttcagctgg   4260
agagaagtcg aggaacagct gattcgctat gtgcacgacg gcagtgagac tctgaccgat   4320
tcattcgtgc tggtcgcaaa cgccagcgaa atggaccggc agtcccatcc agtcgccttt   4380
acagtgacta tcctgcccgt gaacgatcag ccacccattc tgacaactaa tacagggctg   4440
cagatgtggg aaggagccac tgtgcctatc ccagctgagg cactgagaag taccgacggg   4500
gattcaggac ctgaggacct ggtgtacaca attgaacagc caagcaatgg acgagtggtc   4560
ctgcgagcag ctccaggaac tgaggtgagg tctttcaccc aggcacagct ggatggggga   4620
ctggtgctgt ttagtcaccg aggcgctctg gacggcgggt tcaggttttc tctgagtgat   4680
ggcgagcaca cctcccctgg gcatttcttt agagtcacag cccagaagca ggtgctgctg   4740
tcactggaag ggagcaggac cctgacagtc tgcccaggat ctgtgcagcc cctgtctagt   4800
cagagtctgc gagcatcaag ctccgccgga accgaccctc accatctgct gtatagagtg   4860 gtcagggac cacagctggg acggctgttc catgcacagc agggcagcac aggggaagcc    4920
```

-continued

```
ctggtgaact ttactcaggc tgaggtctac gcaggcaatg tgctgtatga gcacgaaatg    4980
cctccagaac ccttctggga ggcccatgac accctggagc tgcagctgtc tagtcccct     5040
gctcctgatg tggcagccac actggccgtg gctgtctcct ttgaggctgc atgtccacag    5100
cgcccctctc gactgtggaa gaacaaagga ctgtgggtgc cagaaggaca gcgagcagag    5160
atcaccgtgg ccgctctgga cgcctccaat ctgctggctt ctgtgcccag tcctcagcgg    5220
ccagagcacg atgtcctgtt ccaagtgact cagtttccca ccagaggaca gctgctggtg    5280
tcagaggaac cactgcacgc aggcaggcct catttcctgc agagcgagct ggcagcagga    5340
cagctggtgt acgcacacgg aggcggggga acccagcagg acggcttcag gtttcgcgca    5400
catctgcagg gacctgcagg agcatcagtg gctggaccac agactagcga agcttttgca    5460
atcaccgtgc gagatgtcaa cgagcggcca ccccagcctc aggcaagcgt gccactgcga    5520
ctgacaagag ggagcagggc acctatctcc agagcccagc tgtctgtggt cgaccccgat    5580
agcgcacctg gagagattga atatgaggtg cagagggccc cacacaacgg attcctgtcc    5640
ctggtcggcg ggggaccagg accagtgact cggttcaccc aggcagacgt ggatgctggc    5700
aggctggcat tcgtcgccaa tggctcaagc gtggctggga tctttcagct gtcaatgagc    5760
gacggggcat ctcctccact gcctatgagt ctggcagtgg atgtcctgcc atccgccatt    5820
gaggtccagc tgcgagctcc actggaagtg ccacaggcac tgggccggtc ctctctgtca    5880
cggcagcagc tgagagtggt cagcgaccgc gaggaacccg atgctgcata ccggctgatc    5940
cagggccctc agtatggaca cctgctggtg ggcgggcagc cagcatcagc tttcagccag    6000
ctgcaggtgg accagggaga ggtggtcttc gcctttacca acttcagttc aagccacgat    6060
cattttttcag tcctggcact ggccagagga gtgaacgcta gcgcaacagt gaatgtcact    6120
gtgagggccc tgctgcacgt gtgggctgga ggcccttggc cacagggagc cacactgcga    6180
ctggacccta ctgtgctgga tgcaggagag ctggcaaatc gaaccggcag cgtgccacga    6240
ttccggctgc tggcaggacc tcgacatgga cgagtggtcc gggtgccaag agctaggact    6300
gagcccggcg gcagccagct ggtggaacag tttacccagc aggacctgga ggatgggcgg    6360
ctgggactga agtggggag gcctgaggga cgagctccag gacctgcagg ggacagtctg    6420
acactggagc tgtgggcaca gggagtgcct cccgcagtgg cttcactgga tttcgctact    6480
gaaccttaca cgccgctag accatatagt gtcgccctgc tgtcagtgcc agaagcagcc    6540
aggactgagg ctgggaaacc cgaatcctct actcctaccg gagagccagg ccccatggct    6600
agttcacctg tgccaaccgt cgcaaagggc gggttcctgg gatttctgga ggccaatatg    6660
ttcagcgtga tcattccagt gtgcctggtc ctgctgctgc tggccctgat cctgcccctg    6720
ctgtttttacc tcgcaagcg aaacaaagcc ggaaagcacg acgtgcaggt gctggctgca    6780
aaacctagaa atgggctggc cggagatgca gaggccttca ggaaggtgga accaggccag    6840
gctattcccc tggccgctgt gcctgggcag ggagcagccg ctggaggcca ggccgaccca    6900
gagctgctgc agttttgtag agcccctaat cccgccctga gaatggaca gtattgggtc    6960
```

<210> SEQ ID NO 2
<211> LENGTH: 2320
<212> TYPE: PRT
<213> ORGANISM: Artificial Sequence
<220> FEATURE:
<223> OTHER INFORMATION: Synthetic consensus CSPG4

<400> SEQUENCE: 2

Gln Ser Gly Pro Arg Pro Pro Leu Pro Ala Pro Ala Leu Ala Leu Ala

-continued

```
  1               5                  10                 15
Leu Thr Leu Ala Met Leu Ala Arg Ala Ser Ala Ala Ser Phe Phe Gly
            20                  25                 30
Glu Asn His Leu Glu Val Pro Val Ala Thr Ala Leu Thr Asp Ile Asp
            35                  40                 45
Leu Gln Leu Gln Phe Ser Thr Ser Gln Pro Glu Ala Leu Leu Leu Leu
 50                  55                 60
Ala Ala Gly Pro Ala Asp His Leu Leu Leu Gln Leu Tyr Ser Gly Arg
 65                  70                 75                 80
Leu Gln Val Arg Leu Val Leu Gly Gln Glu Leu Arg Leu Gln Thr
            85                  90                 95
Pro Ala Glu Thr Leu Leu Ser Asp Ser Val Pro His Thr Val Val Leu
            100                 105                110
Thr Val Ser Asp Ser Trp Ala Thr Leu Ser Val Asp Gly Leu Leu Asn
            115                 120                125
Ala Ser Ala Pro Val Pro Gly Ala Pro Leu Glu Val Pro Tyr Gly Leu
 130                 135                140
Phe Val Gly Gly Thr Gly Ser Leu Gly Leu Pro Tyr Leu Arg Gly Thr
 145                 150                155                160
Ser Arg Pro Leu Arg Gly Cys Leu His Ala Ala Thr Leu Asn Gly Arg
            165                 170                175
Ser Leu Leu Arg Pro Leu Thr Pro Asp Val His Glu Gly Cys Ala Glu
            180                 185                190
Glu Phe Ser Ala Gly Asp Asp Val Ala Leu Gly Phe Ser Gly Pro His
            195                 200                205
Ser Leu Ala Ala Phe Pro Ala Trp Gly Thr Gln Asp Glu Gly Thr Leu
 210                 215                220
Glu Phe Thr Leu Thr Thr Arg Ser Arg Gln Ala Pro Leu Ala Phe Gln
 225                 230                235                240
Ala Gly Gly Arg His Gly Asp Phe Ile Tyr Val Asp Ile Phe Glu Gly
            245                 250                255
His Leu Arg Ala Val Val Glu Lys Gly Gln Gly Thr Val Leu Leu His
            260                 265                270
Asn Ser Val Pro Val Ala Asp Gly Gln Pro His Glu Val Ser Val His
            275                 280                285
Ile Asp Ala His Arg Leu Glu Ile Ser Val Asp Gln Tyr Pro Thr Arg
 290                 295                300
Thr Ser Asn Arg Gly Val Leu Ser Tyr Leu Glu Pro Arg Gly Ser Leu
 305                 310                315                320
Leu Leu Gly Gly Leu Asp Ala Glu Ala Ser Arg His Leu Gln Glu His
            325                 330                335
Arg Leu Gly Leu Ala Pro Glu Ala Thr Asn Ala Ser Leu Leu Gly Cys
            340                 345                350
Met Glu Asp Leu Ser Val Asn Gly Gln Arg Arg Gly Leu Arg Glu Ala
            355                 360                365
Leu Leu Thr Arg Asn Met Ala Ala Gly Cys Arg Leu Glu Glu Glu Glu
            370                 375                380
Tyr Glu Glu Asp Ala Tyr Gly Pro Tyr Glu Ala Phe Ser Thr Leu Ala
 385                 390                395                400
Pro Glu Ala Trp Pro Ala Met Glu Leu Pro Glu Pro Cys Val Pro Glu
            405                 410                415
Pro Gly Leu Pro Pro Val Phe Ala Asn Phe Thr Gln Leu Leu Thr Ile
            420                 425                430
```

-continued

```
Ser Pro Leu Val Val Ala Glu Gly Gly Thr Ala Trp Leu Glu Trp Arg
        435                 440                 445

His Val Gln Pro Thr Leu Asp Leu Ser Glu Ala Glu Leu Arg Lys Ser
450                 455                 460

Gln Val Leu Phe Ser Val Thr Arg Gly Ala Arg His Gly Glu Leu Glu
465                 470                 475                 480

Leu Asp Ile Pro Gly Ala Gln Ala Arg Lys Met Phe Thr Leu Leu Asp
                485                 490                 495

Val Val Asn Arg Lys Ala Arg Phe Val His Asp Gly Ser Glu Asp Thr
                500                 505                 510

Ser Asp Gln Leu Val Leu Glu Val Ser Val Thr Ala Arg Gly Pro Met
            515                 520                 525

Pro Ser Cys Leu Arg Arg Gly Gln Thr Tyr Leu Leu Pro Ile Gln Val
        530                 535                 540

Asn Pro Val Asn Asp Pro Pro Arg Ile Ile Phe Pro His Gly Ser Leu
545                 550                 555                 560

Met Val Ile Leu Glu His Thr Gln Lys Pro Leu Gly Pro Glu Val Phe
                565                 570                 575

Gln Ala Tyr Asp Pro Asp Ser Ala Cys Glu Gly Leu Thr Phe Gln Leu
                580                 585                 590

Leu Gly Thr Pro Ser Gly Leu Pro Val Glu Arg Arg Asp Gln Pro Gly
            595                 600                 605

Glu Pro Ala Thr Glu Phe Ser Cys Arg Glu Leu Glu Ala Gly Ser Leu
        610                 615                 620

Val Tyr Val His Arg Gly Gly Pro Ala Gln Asp Leu Thr Phe Arg Val
625                 630                 635                 640

Ser Asp Gly Leu Gln Ala Ser Pro Pro Ala Thr Leu Lys Val Val Ala
                645                 650                 655

Val Arg Pro Ala Ile Gln Ile Arg His Ser Thr Gly Leu Arg Leu Ala
                660                 665                 670

Gln Gly Ser Ala Ala Pro Ile Leu Pro Ala Asn Leu Ser Val Glu Thr
            675                 680                 685

Asn Ala Val Gly Gln Asp Val Ser Val Leu Phe Arg Val Thr Gly Ala
        690                 695                 700

Leu Gln Phe Gly Glu Leu Gln Lys Gln Gly Ala Gly Gly Val Glu Gly
705                 710                 715                 720

Ala Glu Trp Trp Ala Thr Gln Ala Phe His Gln Arg Asp Val Glu Gln
                725                 730                 735

Gly Arg Val Arg Tyr Leu Ser Thr Asp Pro Gln His Arg Ala Glu Asp
                740                 745                 750

Thr Val Glu Asn Leu Ala Leu Glu Val Gln Val Gly Gln Glu Thr Leu
            755                 760                 765

Ser Asn Leu Ser Phe Pro Val Thr Ile Gln Arg Ala Thr Val Trp Met
        770                 775                 780

Leu Arg Leu Glu Pro Leu His Thr Gln Asn Thr Gln Gln Glu Ala Leu
785                 790                 795                 800

Thr Thr Ala His Leu Glu Ala Thr Leu Glu Glu Ala Gly Pro Ser Pro
                805                 810                 815

Pro Thr Phe His Tyr Glu Val Val Gln Ala Pro Arg Lys Gly Asn Leu
                820                 825                 830

Gln Leu Gln Gly Thr Arg Leu Ser Asp Gly Gln Gly Phe Thr Gln Asp
            835                 840                 845
```

```
Asp Leu Gln Ala Gly Arg Val Thr Tyr Gly Ala Thr Ala Arg Ala Ser
    850                 855                 860

Glu Ala Val Glu Asp Thr Phe Arg Phe Arg Val Thr Ala Pro Pro His
865                 870                 875                 880

Phe Ser Pro Leu Tyr Thr Phe Pro Ile His Ile Gly Gly Asp Pro Asp
                885                 890                 895

Ala Pro Val Leu Thr Asn Val Leu Ser Val Pro Glu Gly Gly Glu
            900                 905                 910

Gly Val Leu Ser Ala Asp His Leu Phe Val Lys Ser Leu Asn Ser Ala
            915                 920                 925

Ser Tyr Leu Tyr Glu Val Met Glu Arg Pro Arg His Gly Arg Leu Ala
    930                 935                 940

Trp Arg Gly Thr Gln Asp Lys Thr Thr Met Val Thr Ser Phe Thr Asn
945                 950                 955                 960

Glu Asp Leu Leu Arg Gly Arg Leu Val Tyr Gln His Asp Asp Ser Glu
                965                 970                 975

Thr Thr Glu Asp Asp Ile Pro Phe Val Ala Thr Arg Gln Gly Glu Gly
            980                 985                 990

Ser Gly Asp Met Ala Trp Glu Glu Val Arg Gly Val Phe Arg Val Ala
    995                 1000                1005

Ile Gln Pro Val Asn Asp His Ala Pro Val Gln Thr Ile Ser Arg
    1010                1015                1020

Val Phe His Val Ala Arg Gly Gly Arg Arg Leu Leu Thr Thr Asp
    1025                1030                1035

Asp Val Ala Phe Ser Asp Ala Asp Ser Gly Phe Ala Asp Ala Gln
    1040                1045                1050

Leu Val Leu Thr Arg Lys Asp Leu Leu Phe Gly Ser Ile Val Ala
    1055                1060                1065

Val Asp Glu Pro Thr Arg Pro Ile Tyr Arg Phe Thr Gln Glu Asp
    1070                1075                1080

Leu Arg Lys Arg Arg Val Leu Phe Val His Ser Gly Ala Asp Arg
    1085                1090                1095

Gly Trp Ile Gln Leu Gln Val Ser Asp Gly Gln His Gln Ala Thr
    1100                1105                1110

Ala Leu Leu Glu Val Gln Ala Ser Glu Pro Tyr Leu Arg Val Ala
    1115                1120                1125

Asn Gly Ser Ser Leu Val Val Pro Gln Gly Gly Gln Gly Thr Ile
    1130                1135                1140

Asp Thr Ala Val Leu His Leu Asp Thr Asn Leu Asp Ile Arg Ser
    1145                1150                1155

Gly Asp Glu Val His Tyr His Val Thr Ala Gly Pro Arg Trp Gly
    1160                1165                1170

Gln Leu Leu Arg Ala Gly Gln Pro Ala Thr Ala Phe Ser Gln Gln
    1175                1180                1185

Asp Leu Leu Asp Gly Ala Ile Leu Tyr Ser His Asn Gly Ser Leu
    1190                1195                1200

Ser Pro Arg Asp Thr Leu Ala Phe Ser Val Glu Ala Gly Pro Val
    1205                1210                1215

His Thr Asp Ala Thr Leu Gln Val Thr Ile Ala Leu Glu Gly Pro
    1220                1225                1230

Leu Ala Pro Leu His Leu Val Gln His Lys Lys Ile Tyr Val Phe
    1235                1240                1245

Gln Gly Glu Ala Ala Glu Ile Arg Arg Asp Gln Leu Glu Ala Ala
```

```
            1250                1255                1260

Gln Glu Ala Val Pro Pro Ala Asp Ile Val Phe Ser Val Lys Thr
    1265                1270                1275

Pro Pro Ser Ala Gly Tyr Leu Val Met Val Ser His Gly Ala Leu
    1280                1285                1290

Ala Asp Glu Pro Pro Ser Leu Asp Pro Val Gln Ser Phe Ser Gln
    1295                1300                1305

Glu Ala Val Asp Ala Gly Arg Val Leu Tyr Leu His Ser Arg Pro
    1310                1315                1320

Glu Ala Trp Ser Asp Ala Phe Ser Leu Asp Val Ala Ser Gly Leu
    1325                1330                1335

Gly Ala Pro Leu Glu Gly Val Leu Val Glu Leu Glu Val Leu Pro
    1340                1345                1350

Ala Ala Ile Pro Leu Glu Ala Gln Asn Phe Ser Val Pro Glu Gly
    1355                1360                1365

Gly Ser Arg Thr Leu Ala Pro Pro Leu Leu Arg Val Thr Gly Pro
    1370                1375                1380

Tyr Phe Pro Thr Leu Pro Gly Leu Ser Leu Gln Val Leu Glu Pro
    1385                1390                1395

Pro Gln His Gly Ala Leu Gln Arg Glu Glu Gly Pro Gln Asp Arg
    1400                1405                1410

Thr Leu Ser Ala Phe Ser Trp Arg Glu Val Glu Glu Gln Leu Ile
    1415                1420                1425

Arg Tyr Val His Asp Gly Ser Glu Thr Leu Thr Asp Ser Phe Val
    1430                1435                1440

Leu Val Ala Asn Ala Ser Glu Met Asp Arg Gln Ser His Pro Val
    1445                1450                1455

Ala Phe Thr Val Thr Ile Leu Pro Val Asn Asp Gln Pro Pro Ile
    1460                1465                1470

Leu Thr Thr Asn Thr Gly Leu Gln Met Trp Glu Gly Ala Thr Val
    1475                1480                1485

Pro Ile Pro Ala Glu Ala Leu Arg Ser Thr Asp Gly Asp Ser Gly
    1490                1495                1500

Pro Glu Asp Leu Val Tyr Thr Ile Glu Gln Pro Ser Asn Gly Arg
    1505                1510                1515

Val Val Leu Arg Ala Ala Pro Gly Thr Glu Val Arg Ser Phe Thr
    1520                1525                1530

Gln Ala Gln Leu Asp Gly Gly Leu Val Leu Phe Ser His Arg Gly
    1535                1540                1545

Ala Leu Asp Gly Gly Phe Arg Phe Ser Leu Ser Asp Gly Glu His
    1550                1555                1560

Thr Ser Pro Gly His Phe Phe Arg Val Thr Ala Gln Lys Gln Val
    1565                1570                1575

Leu Leu Ser Leu Glu Gly Ser Arg Thr Leu Thr Val Cys Pro Gly
    1580                1585                1590

Ser Val Gln Pro Leu Ser Ser Gln Ser Leu Arg Ala Ser Ser Ser
    1595                1600                1605

Ala Gly Thr Asp Pro His His Leu Leu Tyr Arg Val Val Arg Gly
    1610                1615                1620

Pro Gln Leu Gly Arg Leu Phe His Ala Gln Gln Gly Ser Thr Gly
    1625                1630                1635

Glu Ala Leu Val Asn Phe Thr Gln Ala Glu Val Tyr Ala Gly Asn
    1640                1645                1650
```

```
Val Leu Tyr Glu His Glu Met Pro Pro Glu Pro Phe Trp Glu Ala
    1655                1660            1665

His Asp Thr Leu Glu Leu Gln Leu Ser Ser Pro Pro Ala Pro Asp
    1670                1675            1680

Val Ala Ala Thr Leu Ala Val Ala Val Ser Phe Glu Ala Ala Cys
    1685                1690            1695

Pro Gln Arg Pro Ser Arg Leu Trp Lys Asn Lys Gly Leu Trp Val
    1700                1705            1710

Pro Glu Gly Gln Arg Ala Glu Ile Thr Val Ala Ala Leu Asp Ala
    1715                1720            1725

Ser Asn Leu Leu Ala Ser Val Pro Ser Pro Gln Arg Pro Glu His
    1730                1735            1740

Asp Val Leu Phe Gln Val Thr Gln Phe Pro Thr Arg Gly Gln Leu
    1745                1750            1755

Leu Val Ser Glu Glu Pro Leu His Ala Gly Arg Pro His Phe Leu
    1760                1765            1770

Gln Ser Glu Leu Ala Ala Gly Gln Leu Val Tyr Ala His Gly Gly
    1775                1780            1785

Gly Gly Thr Gln Gln Asp Gly Phe Arg Phe Arg Ala His Leu Gln
    1790                1795            1800

Gly Pro Ala Gly Ala Ser Val Ala Gly Pro Gln Thr Ser Glu Ala
    1805                1810            1815

Phe Ala Ile Thr Val Arg Asp Val Asn Glu Arg Pro Pro Gln Pro
    1820                1825            1830

Gln Ala Ser Val Pro Leu Arg Leu Thr Arg Gly Ser Arg Ala Pro
    1835                1840            1845

Ile Ser Arg Ala Gln Leu Ser Val Val Asp Pro Asp Ser Ala Pro
    1850                1855            1860

Gly Glu Ile Glu Tyr Glu Val Gln Arg Ala Pro His Asn Gly Phe
    1865                1870            1875

Leu Ser Leu Val Gly Gly Gly Pro Gly Pro Val Thr Arg Phe Thr
    1880                1885            1890

Gln Ala Asp Val Asp Ala Gly Arg Leu Ala Phe Val Ala Asn Gly
    1895                1900            1905

Ser Ser Val Ala Gly Ile Phe Gln Leu Ser Met Ser Asp Gly Ala
    1910                1915            1920

Ser Pro Pro Leu Pro Met Ser Leu Ala Val Asp Val Leu Pro Ser
    1925                1930            1935

Ala Ile Glu Val Gln Leu Arg Ala Pro Leu Glu Val Pro Gln Ala
    1940                1945            1950

Leu Gly Arg Ser Ser Leu Ser Arg Gln Gln Leu Arg Val Val Ser
    1955                1960            1965

Asp Arg Glu Glu Pro Asp Ala Ala Tyr Arg Leu Ile Gln Gly Pro
    1970                1975            1980

Gln Tyr Gly His Leu Leu Val Gly Gly Gln Pro Ala Ser Ala Phe
    1985                1990            1995

Ser Gln Leu Gln Val Asp Gln Gly Glu Val Val Phe Ala Phe Thr
    2000                2005            2010

Asn Phe Ser Ser Ser His Asp His Phe Ser Val Leu Ala Leu Ala
    2015                2020            2025

Arg Gly Val Asn Ala Ser Ala Thr Val Asn Val Thr Val Arg Ala
    2030                2035            2040
```

Leu Leu His Val Trp Ala Gly Gly Pro Trp Pro Gln Gly Ala Thr
    2045                2050                2055

Leu Arg Leu Asp Pro Thr Val Leu Asp Ala Gly Glu Leu Ala Asn
    2060                2065                2070

Arg Thr Gly Ser Val Pro Arg Phe Arg Leu Leu Ala Gly Pro Arg
    2075                2080                2085

His Gly Arg Val Val Arg Val Pro Arg Ala Arg Thr Glu Pro Gly
    2090                2095                2100

Gly Ser Gln Leu Val Glu Gln Phe Thr Gln Gln Asp Leu Glu Asp
    2105                2110                2115

Gly Arg Leu Gly Leu Glu Val Gly Arg Pro Glu Gly Arg Ala Pro
    2120                2125                2130

Gly Pro Ala Gly Asp Ser Leu Thr Leu Glu Leu Trp Ala Gln Gly
    2135                2140                2145

Val Pro Pro Ala Val Ala Ser Leu Asp Phe Ala Thr Glu Pro Tyr
    2150                2155                2160

Asn Ala Ala Arg Pro Tyr Ser Val Ala Leu Leu Ser Val Pro Glu
    2165                2170                2175

Ala Ala Arg Thr Glu Ala Gly Lys Pro Glu Ser Ser Thr Pro Thr
    2180                2185                2190

Gly Glu Pro Gly Pro Met Ala Ser Ser Pro Val Pro Thr Val Ala
    2195                2200                2205

Lys Gly Gly Phe Leu Gly Phe Leu Glu Ala Asn Met Phe Ser Val
    2210                2215                2220

Ile Ile Pro Val Cys Leu Val Leu Leu Leu Ala Leu Ile Leu
    2225                2230                2235

Pro Leu Leu Phe Tyr Leu Arg Lys Arg Asn Lys Ala Gly Lys His
    2240                2245                2250

Asp Val Gln Val Leu Ala Ala Lys Pro Arg Asn Gly Leu Ala Gly
    2255                2260                2265

Asp Ala Glu Ala Phe Arg Lys Val Glu Pro Gly Gln Ala Ile Pro
    2270                2275                2280

Leu Ala Ala Val Pro Gly Gln Gly Ala Ala Ala Gly Gly Gln Ala
    2285                2290                2295

Asp Pro Glu Leu Leu Gln Phe Cys Arg Ala Pro Asn Pro Ala Leu
    2300                2305                2310

Lys Asn Gly Gln Tyr Trp Val
    2315                2320

<210> SEQ ID NO 3
<211> LENGTH: 7020
<212> TYPE: DNA
<213> ORGANISM: Artificial Sequence
<220> FEATURE:
<223> OTHER INFORMATION: Synthetic consensus CSPG4 operably linked to
      IgE leader sequence

<400> SEQUENCE: 3
atggattgga cctggattct gtttctggtg ccgccgcta caagagtgca ttcacagtct      60
ggacctcgac ccctctgcc cgcccctgca ctggccctgg ctctgaccct ggcaatgctg     120
gcaagagcct ccgccgcttc tttctttggc gaaaaccacc tggaggtgcc cgtcgctaca     180
gcactgactg acatcgatct gcagctgcag ttcagcacat cccagccaga ggccctgctg     240
ctgctggcag caggccctgc tgaccatctg ctgctgcagc tgtacagcgg aagactgcag     300
gtcaggctgg tgctgggaca ggaggaactg cgactgcaga caccagccga gactctgctg     360

```
tctgatagtg tcccccacac cgtggtcctg acagtgtcag acagctgggc caccctgtcc    420
gtcgatggac tgctgaacgc atctgctcca gtgccaggag cccctctgga ggtcccatac    480
ggactgttcg tgggcgggac aggctctctg ggactgccat atctgcgggg gactagtcgg    540
cccctgagag gatgcctgca cgctgcaacc ctgaatggcc gctccctgct gcgaccactg    600
acacctgacg tgcatgaggg ctgtgccgag gaattttctg ctggggacga tgtggcactg    660
ggattctccg gaccacactc tctggcagct tttcctgcct ggggcaccca ggatgaaggg    720
actctggagt tcaccctgac cacaaggtcc cgccaggctc ccctggcatt tcaggccgga    780
ggccgccacg gcgacttcat ctacgtggat attttgagg gcatctgcg ggccgtggtc    840
gaaaaggggc agggaacagt gctgctgcac aactctgtgc cagtcgcaga cggccagccc    900
catgaagtga gtgtccacat cgacgctcat agactggaga tttcagtgga tcagtaccct    960
acccggacaa gcaatagagg ggtgctgtcc tatctggagc caaggggaag cctgctgctg    1020
ggcggcctgg acgcagaggc ctccagacac ctgcaggaac ataggctggg cctggctccc    1080
gaagcaacaa acgcctccct gctggggtgc atggaggatc tgtctgtgaa tggacagcga    1140
agaggactgc gagaggccct gctgactcga acatggcag ccggatgtcg gctggaggaa    1200
gaggaatatg aggaagacgc ttacggccct tatgaggcat tcagcaccct ggctcccgaa    1260
gcatggcctg ccatggaact gcctgagcca tgcgtcccag agcctggact gcctcccgtg    1320
ttcgccaact tcacccagct gctgactatc tctccactgg tggtcgcaga gggcgggact    1380
gcttggctgg aatggcgaca cgtgcagccc accctggacc tgagcgaggc cgaactgcgg    1440
aaatcccagg tgctgttttc tgtcaccagg ggagctcgcc atggcgagct ggaactggat    1500
attcccggag ctcaggcaag aaaaatgttc acactgctgg acgtggtcaa ccgaaaggcc    1560
cggtttgtgc acgatggcag tgaagacaca tcagatcagc tggtgctgga ggtgagtgtc    1620
actgccagag gcccaatgcc ctcatgtctg aggcgcgggc agacctacct gctgcctatc    1680
caggtcaacc cagtgaatga cccacccagg atcatttttcc cacacgggtc cctgatggtc    1740
atcctggagc atacacagaa gccactggga cccgaggtgt tccaggccta tgaccccgat    1800
agcgcctgcg agggcctgac ttttcagctg ctgggaaccc catccggact gccagtggaa    1860
cgacgagatc agcctggcga accagcaacc gagttcagtt gtcgcgagct ggaagccggg    1920
tcactggtgt acgtccacag aggaggccca gcacaggacc tgaccttccg ggtgagcgat    1980
ggcctgcagg ctagtcctcc agcaactctg aaagtggtcg ccgtgcggcc tgctatccag    2040
attagacata gcaccggact gaggctggca cagggctccg ctgcacccat cctgcctgcc    2100
aacctgtctg tcgagaccaa tgctgtgggc caggacgtga tgtcctgtt cagggtgaca    2160
ggagccctga gtttggaga gctgcagaag cagggagcag gggagtgga aggagcagag    2220
tggtgggcta cccaggcatt ccaccagcga gatgtcgagc agggacgagt gcggtacctg    2280
agcaccgacc cccagcatcg ggcagaagat acagtgaga acctggccct ggaggtgcag    2340
gtcggacagg aaacactgag taatctgtca tttcccgtca ccattcagag ggccacagtg    2400
tggatgctgc gcctggagcc tctgcacacc cagaacacac agcaggaggc actgactacc    2460
gcccatctgg aagctactct ggaggaagca ggacctagcc tcccaccttc cactatgag    2520
gtggtccagg ctccacgcaa gggcaatctg cagctgcagg gaactagact gtctgacgga    2580
cagggtttta cccaggacga tctgcaggca ggacgagtga cctacggagc aacagccaga    2640
gccagtgaag ccgtcgagga taccttccgg ttccggtga ctgctccacc ccacttctct    2700
```

```
cccctgtata cttttcctat ccatattggc ggggacccag atgcacccgt gctgaccaac    2760
gtcctgctgt ccgtgccaga aggaggcgag ggcgtcctga gcgcagacca cctgttcgtg    2820
aaatccctga attccgcctc ttacctgtat gaagtgatgg agcgaccacg acatggaagg    2880
ctggcatggc gaggaaccca ggacaagaca actatggtga ctagcttcac caacgaggat    2940
ctgctgcggg gcagactggt gtaccagcac gacgattccg aaaccacaga ggacgatatc    3000 cccttttgtgg ctactagaca gggagagggc tctggggaca tggcatggga ggaagtccga    3060
ggcgtgttcc gggtcgctat ccagcctgtc aatgatcacg caccagtgca gacaattagc    3120
cgcgtgtttc atgtcgcccg aggggggaaga aggctgctga ctaccgacga tgtggcattc    3180
agcgacgccg attccggatt tgccgacgct cagctggtgc tgaccaggaa agatctgctg    3240
ttcggctcca tcgtgccgt cgacgaacct accagaccaa tctacaggtt cacacaggag    3300
gatctgcgca agcgccgagt gctgtttgtc cactccggag cagaccgagg atggattcag    3360
ctgcaggtgt ctgatggcca gcatcaggca ccgccctgc tggaagtcca ggcctctgag    3420
ccctatctgc gcgtggctaa cgggagctcc ctggtggtcc ctcagggcgg gcagggaaca    3480
atcgacactg ccgtgctgca cctggacaca aatctggata ttcggagcgg agatgaggtc    3540
cactaccatg tgactgctgg accacgatgg ggacagctgc tgagagcagg acagccagct    3600
accgcattca gtcagcagga cctgctggat ggagccatcc tgtattcaca caacggcagt    3660
ctgtcaccca gggacactct ggccttcagc gtcgaggcag gacctgtgca taccgatgcc    3720
acactgcagg tgaccattgc tctggaagga cccctggcac ctctgcacct ggtccagcat    3780
aagaaaatct acgtgttcca gggcgaagcc gctgagattc ggagagacca gctggaagca    3840
gcccaggagg ctgtgcctcc agcagatatc gtgttttcag tcaaaacccc tcccagcgcc    3900
ggatacctgt tcatggtgag ccacggagcc ctggctgacg aacccaccag cctgaccccc    3960
gtgcagagct ctcccaggga ggcagtcgac gctggacgag tgctgtatct gcattcccgg    4020
cctgaggcct ggtctgacgc ttttagtctg gatgtggctt ctggactggg cgcaccactg    4080
gaaggggtgc tggtcgagct ggaagtgctg cctgctgcaa tcccactgga ggcccagaat    4140
ttctccgtcc ctgaaggagg ctctcggacc ctggctcctc cactgctgag agtgaccggc    4200
ccatactttc ccacactgcc tggactgtcc ctgcaggtgc tggagccccc tcagcacggc    4260
gccctgcaga gagaggaagg accccaggac aggacactga gcgccttcag ctggagagaa    4320
gtcgaggaac agctgattcg ctatgtgcac gacggcagtg agactctgac cgattcattc    4380
gtgctggtcg caaacgccag cgaaatggac cggcagtccc atccagtcgc ctttacagtg    4440
actatcctgc ccgtgaacga tcagccaccc attctgacaa ctaatacagg gctgcagatg    4500
tgggaaggag ccactgtgcc tatcccagct gaggcactga gaagtaccga cggggattca    4560
ggacctgagg acctggtgta cacaattgaa cagccaagca atggacgagt ggtcctgcga    4620
gcagctccag gaactgaggt gaggtctttc acccaggcac agctggatgg gggactggtg    4680
ctgtttagtc accgaggcgc tctggacggc gggttcaggt tttctctgag tgatggcgag    4740
cacacctccc ctgggcattt ctttagagtc acagcccaga agcaggtgct gctgtcactg    4800
gaagggagca ggaccctgac agtctgccca ggatctgtgc agccctgtc tagtcagagt    4860 ctgcgagcat caagctccgc cggaaccgac cctcaccatc tgctgtatag agtggtcagg    4920
ggaccacagc tgggacggct gttccatgca cagcagggca gcacagggga agccctggtg    4980
aactttactc aggctgaggt ctacgcaggc aatgtgctgt atgagcacga aatgcctcca    5040
gaacccttct gggaggccca tgacaccctg gagctgcagc tgtctagtcc ccctgctcct    5100
```

```
gatgtggcag ccacactggc cgtggctgtc tcctttgagg ctgcatgtcc acagcgcccc    5160
tctcgactgt ggaagaacaa aggactgtgg gtgccagaag acagcgagc agagatcacc    5220 gtggccgctc tggacgcctc caatctgctg gcttctgtgc ccagtcctca gcggccagag    5280
cacgatgtcc tgttccaagt gactcagttt cccaccagag acagctgct ggtgtcagag    5340 gaaccactgc acgcaggcag gcctcatttc ctgcagagcg agctggcagc aggacagctg    5400
gtgtacgcac acggaggcgg gggaacccag caggacggct tcaggtttcg cgcacatctg    5460
cagggacctg caggagcatc agtggctgga ccacagacta gcgaagcttt tgcaatcacc    5520
gtgcgagatg tcaacgagcg gccaccccag cctcaggcaa gcgtgccact gcgactgaca    5580
agagggagca gggcacctat ctccagagcc cagctgtctg tggtcgaccc cgatagcgca    5640
cctggagaga ttgaatatga ggtgcagagg gccccacaca acggattcct gtccctggtc    5700
ggcgggggac caggaccagt gactcggttc acccaggcag acgtggatgc tggcaggctg    5760
gcattcgtcg ccaatggctc aagcgtggct gggatctttc agctgtcaat gagcgacggg    5820
gcatctcctc cactgcctat gagtctggca gtggatgtcc tgccatccgc cattgaggtc    5880
cagctgcgag ctccactgga agtgccacag gcactgggcc ggtcctctct gtcacggcag    5940
cagctgagag tggtcagcga ccgcgaggaa cccgatgctg cataccggct gatccagggc    6000
cctcagtatg acacctgct ggtgggcggg cagccagcat cagctttcag ccagctgcag    6060
gtggaccagg gagaggtggt cttcgccttt accaacttca gttcaagcca cgatcatttt    6120
tcagtcctgg cactgccag aggagtgaac gctagcgcaa cagtgaatgt cactgtgagg    6180
gccctgctgc acgtgtgggc tggaggccct tggccacagg gagccacact gcgactggac    6240
cctactgtgc tggatgcagg agagctggca atcgaaccg gcagcgtgcc acgattccgg    6300
ctgctggcag gacctcgaca tggacgagtg gtccgggtgc aagagctag gactgagccc    6360 ggcggcagcc agctggtgga acagtttacc cagcaggacc tggaggatgg gcggctggga    6420
ctggaagtgg ggaggcctga gggacgagct ccaggacctg caggggacag tctgacactg    6480
gagctgtggg cacagggagt gcctcccgca gtggcttcac tggatttcgc tactgaacct    6540
tacaacgccg ctagaccata tagtgtcgcc ctgctgtcag tgccagaagc agccaggact    6600
gaggctggga aacccgaatc ctctactcct accggagagc caggccccat ggctagttca    6660
cctgtgccaa ccgtcgcaaa gggcgggttc ctgggatttc tggaggccaa tatgttcagc    6720
gtgatcattc cagtgtgcct ggtcctgctg ctgctggccc tgatcctgcc cctgctgttt    6780
tacctgcgca agcgaaacaa agccggaaag cacgacgtgc aggtgctggc tgcaaaacct    6840
agaaatgggc tggccggaga tgcagaggcc ttcaggaagg tggaaccagg ccaggctatt    6900 ccctgccg ctgtgcctgg gcaggagca gccgctggag gccaggccga cccagagctg    6960
ctgcagtttt gtagagcccc taatcccgcc ctgaagaatg gacagtattg ggtctgataa    7020
```

<210> SEQ ID NO 4
<211> LENGTH: 2338
<212> TYPE: PRT
<213> ORGANISM: Artificial Sequence
<220> FEATURE:
<223> OTHER INFORMATION: Synthetic consensus CSPG4 operably linked to
      IgE leader sequence

<400> SEQUENCE: 4

Met Asp Trp Thr Trp Ile Leu Phe Leu Val Ala Ala Ala Thr Arg Val
1               5                   10                  15

```
His Ser Gln Ser Gly Pro Arg Pro Leu Pro Ala Pro Ala Leu Ala
             20                  25                  30

Leu Ala Leu Thr Leu Ala Met Leu Ala Arg Ala Ser Ala Ala Ser Phe
         35                  40                  45

Phe Gly Glu Asn His Leu Glu Val Pro Val Ala Thr Ala Leu Thr Asp
     50                  55                  60

Ile Asp Leu Gln Leu Gln Phe Ser Thr Ser Gln Pro Glu Ala Leu Leu
65                  70                  75                  80

Leu Leu Ala Ala Gly Pro Ala Asp His Leu Leu Gln Leu Tyr Ser
                 85                  90                  95

Gly Arg Leu Gln Val Arg Leu Val Leu Gly Gln Glu Glu Leu Arg Leu
             100                 105                 110

Gln Thr Pro Ala Glu Thr Leu Leu Ser Asp Ser Val Pro His Thr Val
         115                 120                 125

Val Leu Thr Val Ser Asp Ser Trp Ala Thr Leu Ser Val Asp Gly Leu
    130                 135                 140

Leu Asn Ala Ser Ala Pro Val Pro Gly Ala Pro Leu Glu Val Pro Tyr
145                 150                 155                 160

Gly Leu Phe Val Gly Gly Thr Gly Ser Leu Gly Leu Pro Tyr Leu Arg
                165                 170                 175

Gly Thr Ser Arg Pro Leu Arg Gly Cys Leu His Ala Ala Thr Leu Asn
            180                 185                 190

Gly Arg Ser Leu Leu Arg Pro Leu Thr Pro Asp Val His Glu Gly Cys
        195                 200                 205

Ala Glu Glu Phe Ser Ala Gly Asp Asp Val Ala Leu Gly Phe Ser Gly
210                 215                 220

Pro His Ser Leu Ala Ala Phe Pro Ala Trp Gly Thr Gln Asp Glu Gly
225                 230                 235                 240

Thr Leu Glu Phe Thr Leu Thr Thr Arg Ser Arg Gln Ala Pro Leu Ala
                245                 250                 255

Phe Gln Ala Gly Gly Arg His Gly Asp Phe Ile Tyr Val Asp Ile Phe
            260                 265                 270

Glu Gly His Leu Arg Ala Val Val Glu Lys Gly Gln Gly Thr Val Leu
        275                 280                 285

Leu His Asn Ser Val Pro Val Ala Asp Gly Gln Pro His Glu Val Ser
290                 295                 300

Val His Ile Asp Ala His Arg Leu Glu Ile Ser Val Asp Gln Tyr Pro
305                 310                 315                 320

Thr Arg Thr Ser Asn Arg Gly Val Leu Ser Tyr Leu Glu Pro Arg Gly
                325                 330                 335

Ser Leu Leu Leu Gly Gly Leu Asp Ala Glu Ala Ser Arg His Leu Gln
            340                 345                 350

Glu His Arg Leu Gly Leu Ala Pro Glu Ala Thr Asn Ala Ser Leu Leu
        355                 360                 365

Gly Cys Met Glu Asp Leu Ser Val Asn Gly Gln Arg Arg Gly Leu Arg
370                 375                 380

Glu Ala Leu Leu Thr Arg Asn Met Ala Ala Gly Cys Arg Leu Glu Glu
385                 390                 395                 400

Glu Glu Tyr Glu Glu Asp Ala Tyr Gly Pro Tyr Glu Ala Phe Ser Thr
                405                 410                 415

Leu Ala Pro Glu Ala Trp Pro Ala Met Glu Leu Pro Glu Pro Cys Val
            420                 425                 430

Pro Glu Pro Gly Leu Pro Pro Val Phe Ala Asn Phe Thr Gln Leu Leu
```

-continued

```
                435                 440                 445
Thr Ile Ser Pro Leu Val Val Ala Glu Gly Gly Thr Ala Trp Leu Glu
            450                 455                 460

Trp Arg His Val Gln Pro Thr Leu Asp Leu Ser Glu Ala Glu Leu Arg
465                 470                 475                 480

Lys Ser Gln Val Leu Phe Ser Val Thr Arg Gly Ala Arg His Gly Glu
                485                 490                 495

Leu Glu Leu Asp Ile Pro Gly Ala Gln Ala Arg Lys Met Phe Thr Leu
            500                 505                 510

Leu Asp Val Val Asn Arg Lys Ala Arg Phe Val His Asp Gly Ser Glu
        515                 520                 525

Asp Thr Ser Asp Gln Leu Val Leu Glu Val Ser Val Thr Ala Arg Gly
    530                 535                 540

Pro Met Pro Ser Cys Leu Arg Arg Gly Gln Thr Tyr Leu Leu Pro Ile
545                 550                 555                 560

Gln Val Asn Pro Val Asn Asp Pro Pro Arg Ile Ile Phe Pro His Gly
                565                 570                 575

Ser Leu Met Val Ile Leu Glu His Thr Gln Lys Pro Leu Gly Pro Glu
            580                 585                 590

Val Phe Gln Ala Tyr Asp Pro Asp Ser Ala Cys Glu Gly Leu Thr Phe
        595                 600                 605

Gln Leu Leu Gly Thr Pro Ser Gly Leu Pro Val Glu Arg Arg Asp Gln
    610                 615                 620

Pro Gly Glu Pro Ala Thr Glu Phe Ser Cys Arg Glu Leu Glu Ala Gly
625                 630                 635                 640

Ser Leu Val Tyr Val His Arg Gly Gly Pro Ala Gln Asp Leu Thr Phe
                645                 650                 655

Arg Val Ser Asp Gly Leu Gln Ala Ser Pro Pro Ala Thr Leu Lys Val
            660                 665                 670

Val Ala Val Arg Pro Ala Ile Gln Ile Arg His Ser Thr Gly Leu Arg
        675                 680                 685

Leu Ala Gln Gly Ser Ala Ala Pro Ile Leu Pro Ala Asn Leu Ser Val
    690                 695                 700

Glu Thr Asn Ala Val Gly Gln Asp Val Ser Val Leu Phe Arg Val Thr
705                 710                 715                 720

Gly Ala Leu Gln Phe Gly Glu Leu Gln Lys Gln Gly Ala Gly Gly Val
                725                 730                 735

Glu Gly Ala Glu Trp Trp Ala Thr Gln Ala Phe His Gln Arg Asp Val
            740                 745                 750

Glu Gln Gly Arg Val Arg Tyr Leu Ser Thr Asp Pro Gln His Arg Ala
        755                 760                 765

Glu Asp Thr Val Glu Asn Leu Ala Leu Glu Val Gln Val Gly Gln Glu
    770                 775                 780

Thr Leu Ser Asn Leu Ser Phe Pro Val Thr Ile Gln Arg Ala Thr Val
785                 790                 795                 800

Trp Met Leu Arg Leu Glu Pro Leu His Thr Gln Asn Thr Gln Gln Glu
                805                 810                 815

Ala Leu Thr Thr Ala His Leu Glu Ala Thr Leu Glu Glu Ala Gly Pro
            820                 825                 830

Ser Pro Pro Thr Phe His Tyr Glu Val Val Gln Ala Pro Arg Lys Gly
        835                 840                 845

Asn Leu Gln Leu Gln Gly Thr Arg Leu Ser Asp Gly Gln Gly Phe Thr
    850                 855                 860
```

-continued

Gln Asp Asp Leu Gln Ala Gly Arg Val Thr Tyr Gly Ala Thr Ala Arg
865                 870                 875                 880

Ala Ser Glu Ala Val Glu Asp Thr Phe Arg Phe Arg Val Thr Ala Pro
            885                 890                 895

Pro His Phe Ser Pro Leu Tyr Thr Phe Pro Ile His Ile Gly Gly Asp
        900                 905                 910

Pro Asp Ala Pro Val Leu Thr Asn Val Leu Ser Val Pro Glu Gly
    915                 920                 925

Gly Glu Gly Val Leu Ser Ala Asp His Leu Phe Val Lys Ser Leu Asn
930                 935                 940

Ser Ala Ser Tyr Leu Tyr Glu Val Met Glu Arg Pro Arg His Gly Arg
945                 950                 955                 960

Leu Ala Trp Arg Gly Thr Gln Asp Lys Thr Thr Met Val Thr Ser Phe
                965                 970                 975

Thr Asn Glu Asp Leu Leu Arg Gly Arg Leu Val Tyr Gln His Asp Asp
            980                 985                 990

Ser Glu Thr Thr Glu Asp Asp Ile Pro Phe Val Ala Thr Arg Gln Gly
        995                 1000                1005

Glu Gly Ser Gly Asp Met Ala Trp Glu Glu Val Arg Gly Val Phe
    1010                1015                1020

Arg Val Ala Ile Gln Pro Val Asn Asp His Ala Pro Val Gln Thr
1025                1030                1035

Ile Ser Arg Val Phe His Val Ala Arg Gly Gly Arg Arg Leu Leu
1040                1045                1050

Thr Thr Asp Asp Val Ala Phe Ser Asp Ala Asp Ser Gly Phe Ala
1055                1060                1065

Asp Ala Gln Leu Val Leu Thr Arg Lys Asp Leu Leu Phe Gly Ser
1070                1075                1080

Ile Val Ala Val Asp Glu Pro Thr Arg Pro Ile Tyr Arg Phe Thr
1085                1090                1095

Gln Glu Asp Leu Arg Lys Arg Arg Val Leu Phe Val His Ser Gly
1100                1105                1110

Ala Asp Arg Gly Trp Ile Gln Leu Gln Val Ser Asp Gly Gln His
1115                1120                1125

Gln Ala Thr Ala Leu Leu Glu Val Gln Ala Ser Glu Pro Tyr Leu
1130                1135                1140

Arg Val Ala Asn Gly Ser Ser Leu Val Val Pro Gln Gly Gly Gln
1145                1150                1155

Gly Thr Ile Asp Thr Ala Val Leu His Leu Asp Thr Asn Leu Asp
1160                1165                1170

Ile Arg Ser Gly Asp Glu Val His Tyr His Val Thr Ala Gly Pro
1175                1180                1185

Arg Trp Gly Gln Leu Leu Arg Ala Gly Gln Pro Ala Thr Ala Phe
1190                1195                1200

Ser Gln Gln Asp Leu Leu Asp Gly Ala Ile Leu Tyr Ser His Asn
1205                1210                1215

Gly Ser Leu Ser Pro Arg Asp Thr Leu Ala Phe Ser Val Glu Ala
1220                1225                1230

Gly Pro Val His Thr Asp Ala Thr Leu Gln Val Thr Ile Ala Leu
1235                1240                1245

Glu Gly Pro Leu Ala Pro Leu His Leu Val Gln His Lys Lys Ile
1250                1255                1260

```
Tyr Val Phe Gln Gly Glu Ala Glu Ile Arg Arg Asp Gln Leu
1265                1270                1275

Glu Ala Ala Gln Glu Ala Val Pro Pro Ala Asp Ile Val Phe Ser
1280                1285                1290

Val Lys Thr Pro Pro Ser Ala Gly Tyr Leu Val Met Val Ser His
1295                1300                1305

Gly Ala Leu Ala Asp Glu Pro Pro Ser Leu Asp Pro Val Gln Ser
1310                1315                1320

Phe Ser Gln Glu Ala Val Asp Ala Gly Arg Val Leu Tyr Leu His
1325                1330                1335

Ser Arg Pro Glu Ala Trp Ser Asp Ala Phe Ser Leu Asp Val Ala
1340                1345                1350

Ser Gly Leu Gly Ala Pro Leu Glu Gly Val Leu Val Glu Leu Glu
1355                1360                1365

Val Leu Pro Ala Ala Ile Pro Leu Glu Ala Gln Asn Phe Ser Val
1370                1375                1380

Pro Glu Gly Gly Ser Arg Thr Leu Ala Pro Pro Leu Leu Arg Val
1385                1390                1395

Thr Gly Pro Tyr Phe Pro Thr Leu Pro Gly Leu Ser Leu Gln Val
1400                1405                1410

Leu Glu Pro Pro Gln His Gly Ala Leu Gln Arg Glu Glu Gly Pro
1415                1420                1425

Gln Asp Arg Thr Leu Ser Ala Phe Ser Trp Arg Glu Val Glu Glu
1430                1435                1440

Gln Leu Ile Arg Tyr Val His Asp Gly Ser Glu Thr Leu Thr Asp
1445                1450                1455

Ser Phe Val Leu Val Ala Asn Ala Ser Glu Met Asp Arg Gln Ser
1460                1465                1470

His Pro Val Ala Phe Thr Val Thr Ile Leu Pro Val Asn Asp Gln
1475                1480                1485

Pro Pro Ile Leu Thr Thr Asn Thr Gly Leu Gln Met Trp Glu Gly
1490                1495                1500

Ala Thr Val Pro Ile Pro Ala Glu Ala Leu Arg Ser Thr Asp Gly
1505                1510                1515

Asp Ser Gly Pro Glu Asp Leu Val Tyr Thr Ile Glu Gln Pro Ser
1520                1525                1530

Asn Gly Arg Val Val Leu Arg Ala Ala Pro Gly Thr Glu Val Arg
1535                1540                1545

Ser Phe Thr Gln Ala Gln Leu Asp Gly Gly Leu Val Leu Phe Ser
1550                1555                1560

His Arg Gly Ala Leu Asp Gly Gly Phe Arg Phe Ser Leu Ser Asp
1565                1570                1575

Gly Glu His Thr Ser Pro Gly His Phe Phe Arg Val Thr Ala Gln
1580                1585                1590

Lys Gln Val Leu Leu Ser Leu Glu Gly Ser Arg Thr Leu Thr Val
1595                1600                1605

Cys Pro Gly Ser Val Gln Pro Leu Ser Ser Gln Ser Leu Arg Ala
1610                1615                1620

Ser Ser Ser Ala Gly Thr Asp Pro His His Leu Leu Tyr Arg Val
1625                1630                1635

Val Arg Gly Pro Gln Leu Gly Arg Leu Phe His Ala Gln Gln Gly
1640                1645                1650

Ser Thr Gly Glu Ala Leu Val Asn Phe Thr Gln Ala Glu Val Tyr
```

-continued

```
            1655                1660                1665
Ala Gly Asn Val Leu Tyr Glu His Glu Met Pro Pro Glu Pro Phe
    1670                1675                1680

Trp Glu Ala His Asp Thr Leu Glu Leu Gln Leu Ser Ser Pro Pro
    1685                1690                1695

Ala Pro Asp Val Ala Ala Thr Leu Ala Val Ala Val Ser Phe Glu
    1700                1705                1710

Ala Ala Cys Pro Gln Arg Pro Ser Arg Leu Trp Lys Asn Lys Gly
    1715                1720                1725

Leu Trp Val Pro Glu Gly Gln Arg Ala Glu Ile Thr Val Ala Ala
    1730                1735                1740

Leu Asp Ala Ser Asn Leu Leu Ala Ser Val Pro Ser Pro Gln Arg
    1745                1750                1755

Pro Glu His Asp Val Leu Phe Gln Val Thr Gln Phe Pro Thr Arg
    1760                1765                1770

Gly Gln Leu Leu Val Ser Glu Glu Pro Leu His Ala Gly Arg Pro
    1775                1780                1785

His Phe Leu Gln Ser Glu Leu Ala Ala Gly Gln Leu Val Tyr Ala
    1790                1795                1800

His Gly Gly Gly Thr Gln Gln Asp Gly Phe Arg Phe Arg Ala
    1805                1810                1815

His Leu Gln Gly Pro Ala Gly Ala Ser Val Ala Gly Pro Gln Thr
    1820                1825                1830

Ser Glu Ala Phe Ala Ile Thr Val Arg Asp Val Asn Glu Arg Pro
    1835                1840                1845

Pro Gln Pro Gln Ala Ser Val Pro Leu Arg Leu Thr Arg Gly Ser
    1850                1855                1860

Arg Ala Pro Ile Ser Arg Ala Gln Leu Ser Val Val Asp Pro Asp
    1865                1870                1875

Ser Ala Pro Gly Glu Ile Glu Tyr Glu Val Gln Arg Ala Pro His
    1880                1885                1890

Asn Gly Phe Leu Ser Leu Val Gly Gly Gly Pro Gly Pro Val Thr
    1895                1900                1905

Arg Phe Thr Gln Ala Asp Val Asp Ala Gly Arg Leu Ala Phe Val
    1910                1915                1920

Ala Asn Gly Ser Ser Val Ala Gly Ile Phe Gln Leu Ser Met Ser
    1925                1930                1935

Asp Gly Ala Ser Pro Pro Leu Pro Met Ser Leu Ala Val Asp Val
    1940                1945                1950

Leu Pro Ser Ala Ile Glu Val Gln Leu Arg Ala Pro Leu Glu Val
    1955                1960                1965

Pro Gln Ala Leu Gly Arg Ser Ser Leu Ser Arg Gln Gln Leu Arg
    1970                1975                1980

Val Val Ser Asp Arg Glu Glu Pro Asp Ala Ala Tyr Arg Leu Ile
    1985                1990                1995

Gln Gly Pro Gln Tyr Gly His Leu Leu Val Gly Gly Gln Pro Ala
    2000                2005                2010

Ser Ala Phe Ser Gln Leu Gln Val Asp Gln Gly Glu Val Val Phe
    2015                2020                2025

Ala Phe Thr Asn Phe Ser Ser His Asp His Phe Ser Val Leu
    2030                2035                2040

Ala Leu Ala Arg Gly Val Asn Ala Ser Ala Thr Val Asn Val Thr
    2045                2050                2055
```

Val Arg Ala Leu Leu His Val Trp Ala Gly Gly Pro Trp Pro Gln
2060                2065                2070

Gly Ala Thr Leu Arg Leu Asp Pro Thr Val Leu Asp Ala Gly Glu
2075                2080                2085

Leu Ala Asn Arg Thr Gly Ser Val Pro Arg Phe Arg Leu Leu Ala
2090                2095                2100

Gly Pro Arg His Gly Arg Val Val Arg Val Pro Arg Ala Arg Thr
2105                2110                2115

Glu Pro Gly Gly Ser Gln Leu Val Glu Gln Phe Thr Gln Gln Asp
2120                2125                2130

Leu Glu Asp Gly Arg Leu Gly Leu Glu Val Gly Arg Pro Glu Gly
2135                2140                2145

Arg Ala Pro Gly Pro Ala Gly Asp Ser Leu Thr Leu Glu Leu Trp
2150                2155                2160

Ala Gln Gly Val Pro Pro Ala Val Ala Ser Leu Asp Phe Ala Thr
2165                2170                2175

Glu Pro Tyr Asn Ala Ala Arg Pro Tyr Ser Val Ala Leu Leu Ser
2180                2185                2190

Val Pro Glu Ala Ala Arg Thr Glu Ala Gly Lys Pro Glu Ser Ser
2195                2200                2205

Thr Pro Thr Gly Glu Pro Gly Pro Met Ala Ser Ser Pro Val Pro
2210                2215                2220

Thr Val Ala Lys Gly Gly Phe Leu Gly Phe Leu Glu Ala Asn Met
2225                2230                2235

Phe Ser Val Ile Ile Pro Val Cys Leu Val Leu Leu Leu Leu Ala
2240                2245                2250

Leu Ile Leu Pro Leu Leu Phe Tyr Leu Arg Lys Arg Asn Lys Ala
2255                2260                2265

Gly Lys His Asp Val Gln Val Leu Ala Ala Lys Pro Arg Asn Gly
2270                2275                2280

Leu Ala Gly Asp Ala Glu Ala Phe Arg Lys Val Glu Pro Gly Gln
2285                2290                2295

Ala Ile Pro Leu Ala Ala Val Pro Gly Gln Gly Ala Ala Ala Gly
2300                2305                2310

Gly Gln Ala Asp Pro Glu Leu Leu Gln Phe Cys Arg Ala Pro Asn
2315                2320                2325

Pro Ala Leu Lys Asn Gly Gln Tyr Trp Val
2330                2335

<210> SEQ ID NO 5
<211> LENGTH: 9974
<212> TYPE: DNA
<213> ORGANISM: Artificial Sequence
<220> FEATURE:
<223> OTHER INFORMATION: Full plasmid sequence for pGX1416, comprising
      CSPG4 coding DNA sequence

<400> SEQUENCE: 5
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300

```
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catgattgg acctggattc tgtttctggt ggccgccgct    780
acaagagtgc attcacagtc tggacctcga ccccctctgc ccgcccctgc actggccctg    840
gctctgaccc tggcaatgct ggcaagagcc tccgccgctt cttctttgg cgaaaaccac    900
ctggaggtgc ccgtcgctac agcactgact gacatcgatc tgcagctgca gttcagcaca    960
tcccagccag aggccctgct gctgctggca gcaggccctg ctgaccatct gctgctgcag   1020
ctgtacagcg gaagactgca ggtcaggctg gtgctgggac aggaggaact gcgactgcag   1080
acaccagccg agactctgct gtctgatagt gtcccccaca ccgtggtcct gacagtgtca   1140
gacagctggg ccaccctgtc cgtcgatgga ctgctgaacg catctgctcc agtgccagga   1200
gccctctgg aggtcccata cggactgttc gtgggcggga caggctctct gggactgcca   1260
tatctgcggg ggactagtcg gcccctgaga ggatgcctgc acgctgcaac cctgaatggc   1320
cgctccctgc tgcgaccact gacacctgac gtgcatgagg ctgtgccga ggaattttct   1380
gctggggacg atgtggcact gggattctcc ggaccacact ctctggcagc ttttcctgcc   1440
tggggcaccc aggatgaagg gactctggag ttcccctga ccacaaggtc ccgccaggct   1500
cccctggcat ttcaggccgg aggccgccac ggcgacttca tctacgtgga tatttttgag   1560
gggcatctgc gggccgtggt cgaaaagggg cagggaacag tgctgctgca caactctgtg   1620
ccagtcgcag acggccagcc ccatgaagtg agtgtccaca tcgacgctca tagactggag   1680
atttcagtgg atcagtaccc tacccggaca agcaatagag gggtgctgtc ctatctggag   1740
ccaagggaa gcctgctgct gggcggcctg gacgcagagg cctccagaca cctgcaggaa   1800
cataggctgg gcctggctcc cgaagcaaca aacgcctccc tgctggggtg catggaggat   1860
ctgtctgtga atggacagcg aagaggactg cgagaggccc tgctgactcg aaacatggca   1920
gccggatgtc ggctggagga agaggaatat gaggaagacg cttacggccc ttatgaggca   1980
ttcagcaccc tggctcccga agcatggcct gccatggaac tgcctgagcc atgcgtccca   2040
gagcctggac tgcctcccgt gttcgccaac ttcacccagc tgctgactat ctctccactg   2100
gtggtcgcag agggcgggac tgcttggctg aatggcgac acgtgcagcc caccctggac   2160
ctgagcgagg ccgaactgcg gaaatcccag gtgctgtttt ctgtcaccag gggagctcgc   2220
catggcgagc tggaactgga tattcccgga gctcaggcaa gaaaaatgtt cacactgctg   2280
gacgtggtca accgaaaggc ccggtttgtg cacgatggca gtgaagacac atcagatcag   2340
ctggtgctgg aggtgagtgt cactgccaga ggcccaatgc cctcatgtct gaggcgcggg   2400
cagacctacc tgctgcctat ccaggtcaac ccagtgaatg acccacccag gatcattttc   2460
ccacacgggt ccctgatggt catcctggag catacacaga agccactggg acccgaggtg   2520
ttccaggcct atgacccga tagcgcctgc gagggcctga cttttcagct gctgggaacc   2580
ccatccggac tgccagtgga acgacgagat cagcctggcg aaccagcaac cgagttcagt   2640
tgtcgcgagc tggaagccgg gtcactggtg tacgtccaca gaggaggccc agcacaggac   2700
```

```
ctgaccttcc gggtgagcga tggcctgcag gctagtcctc cagcaactct gaaagtggtc    2760
gccgtgcggc ctgctatcca gattagacat agcaccggac tgaggctggc acagggctcc    2820
gctgcaccca tcctgcctgc caacctgtct gtcgagacca atgctgtggg ccaggacgtg    2880
agtgtcctgt tcagggtgac aggagccctg cagtttggag agctgcagaa gcagggagca    2940
gggggagtgg aaggagcaga gtggtgggct acccaggcat tccaccagcg agatgtcgag    3000
cagggacgag tgcggtacct gagcaccgac ccccagcatc gggcagaaga tacagtggag    3060
aacctggccc tggaggtgca ggtcggacag gaaacactga gtaatctgtc atttcccgtc    3120
accattcaga gggccacagt gtggatgctg cgcctggagc tctgcacac ccagaacaca    3180 cagcaggagg cactgactac cgcccatctg gaagctactc tggaggaagc aggacctagc    3240
cctcccacct tccactatga ggtggtccag gctccacgca agggcaatct gcagctgcag    3300
ggaactagac tgtctgacgg acaggggttt acccaggacg atctgcaggc aggacgagtg    3360
acctacggaa caacagccag agccagtgaa gccgtcgagg ataccttccg gttccgggtg    3420
actgctccac cccacttctc tcccctgtat acttttccta tccatattgg cggggaccca    3480
gatgcacccg tgctgaccaa cgtcctgctg tccgtgccag aaggaggcga gggcgtcctg    3540
agcgcagacc acctgttcgt gaaatccctg aattccgcct cttacctgta tgaagtgatg    3600
gagcgaccac gacatggaag gctggcatgg cgaggaaccc aggacaagac aactatggtg    3660
actagcttca ccaacgagga tctgctgcgg ggcagactgg tgtaccagca cgacgattcc    3720
gaaaccacag aggacgatat cccctttgtg gctactagac agggagaggg ctctggggac    3780
atggcatggg aggaagtccg aggcgtgttc cgggtcgcta tccagcctgt caatgatcac    3840
gcaccagtgc agacaattag ccgcgtgttt catgtcgccc gagggggaag aaggctgctg    3900
actaccgacg atgtggcatt cagcgacgcc gattccggat ttgccgacgc tcagctggtg    3960
ctgaccagga aagatctgct gttcggctcc atcgtggccg tcgacgaacc taccagacca    4020
atctacaggt tcacacagga ggatctgcgc aagcgccgag tgctgtttgt ccactccgga    4080
gcagaccgag gatggattca gctgcaggtg tctgatggcc agcatcaggc aaccgccctg    4140
ctggaagtcc aggcctctga gccctatctg cgcgtggcta cgggagctc cctggtggtc    4200 cctcagggcg ggcagggaac aatcgacact gccgtgctgc acctggacac aaatctggat    4260
attcggagcg gagatgaggt ccactaccat gtgactgctg gaccacgatg gggacagctg    4320
ctgagagcag gacagccagc taccgcattc agtcagcagg acctgctgga tggagccatc    4380
ctgtattcac acaacggcag tctgtcaccc agggacactc tggccttcag cgtcgaggca    4440
ggacctgtgc ataccgatgc cacactgcag gtgaccattg ctctggaagg acccctggca    4500
cctctgcacc tggtccagca taagaaaatc tacgtgttcc agggcgaagc cgctgagatt    4560
cggagagacc agctggaagc agcccaggag gctgtgcctc cagcagatat cgtgttttca    4620
gtcaaaaccc ctcccagcgc cggatacctg gtcatggtga ccacggagc cctggctgac    4680 gaaccaccca gcctggaccc cgtgcagagc ttctcccagg aggcagtcga cgctggacga    4740
gtgctgtatc tgcattcccg gcctgaggcc tggtctgacg cttttagtct ggatgtggct    4800
tctggactgg gcgcaccact ggaagggggtg ctggtcgagc tggaagtgct gcctgctgca    4860
atcccactgg aggcccagaa tttctccgtc cctgaaggag gctctcggac cctggctcct    4920
ccactgctga gagtgaccgg cccatacttt cccacactgc ctggactgtc cctgcaggtg    4980
ctggagcccc ctcagcacgg cgccctgcag agagaggaag accccagga caggacactg    5040
```

```
agcgccttca gctggagaga agtcgaggaa cagctgattc gctatgtgca cgacggcagt    5100
gagactctga ccgattcatt cgtgctggtc gcaaacgcca gcgaaatgga ccggcagtcc    5160
catccagtcg cctttacagt gactatcctg cccgtgaacg atcagccacc cattctgaca    5220
actaatacag ggctgcagat gtgggaagga gccactgtgc ctatcccagc tgaggcactg    5280
agaagtaccg acggggattc aggacctgag gacctggtgt acacaattga acagccaagc    5340
aatggacgag tggtcctgcg agcagctcca ggaactgagg tgaggtcttt cacccaggca    5400
cagctggatg ggggactggt gctgtttagt caccgaggcg ctctggacgg cgggttcagg    5460
tttctctga gtgatggcga gcacacctcc cctgggcatt tctttagagt cacagcccag    5520
aagcaggtgc tgctgtcact ggaagggagc aggaccctga cagtctgccc aggatctgtg    5580
cagcccctgt ctagtcagag tctgcgagca tcaagctccg ccggaaccga ccctcaccat    5640
ctgctgtata gagtggtcag gggaccacag ctgggacggc tgttccatgc acagcagggc    5700
agcacagggg aagccctggt gaactttact caggctgagg tctacgcagg caatgtgctg    5760
tatgagcacg aaatgcctcc agaacccttc tgggaggccc atgacaccct ggagctgcag    5820
ctgtctagtc cccctgctcc tgatgtggca gccacactgg ccgtggctgt ctcctttgag    5880
gctgcatgtc cacagcgccc ctctcgactg tggaagaaca aaggactgtg ggtgccagaa    5940
ggacagcgag cagagatcac cgtggccgct ctggacgcct ccaatctgct ggcttctgtg    6000
cccagtcctc agcggccaga gcacgatgtc ctgttccaag tgactcagtt cccaccagaa    6060
ggacagctgc tggtgtcaga ggaaccactg cacgcaggca ggcctcattt cctgcagagc    6120
gagctggcag caggacagct ggtgtacgca cacggaggcg ggggaaccca gcaggacggc    6180
ttcaggtttc gcgcacatct gcagggacct gcaggagcat cagtggctgg accacagact    6240
agcgaagctt ttgcaatcac cgtgcgagat gtcaacgagc ggccacccca gcctcaggca    6300
agcgtgccac tgcgactgac aagagggagc agggcaccta tctccagagc ccagctgtct    6360
gtggtcgacc ccgatagcgc acctggagag attgaatatg aggtgcagag ggccccacac    6420
aacggattcc tgtccctggt cggcggggga ccaggaccag tgactcggtt cacccaggca    6480
gacgtggatg ctggcaggct ggcattcgtc gccaatggct caagcgtggc tgggatcttt    6540
cagctgtcaa tgagcgacgg ggcatctcct ccactgccta tgagtctggc agtggatgtc    6600
ctgccatccg ccattgaggt ccagctgcga gctccactgg aagtgccaca ggcactgggc    6660
cggtcctctc tgtcacggca gcagctgaga gtggtcagcg accgcgagga acccgatgct    6720
gcataccggc tgatccaggg ccctcagtat ggacacctgc tggtgggcgg gcagccagca    6780
tcagctttca gccagctgca ggtggaccag ggagaggtgg tcttcgcctt taccaacttc    6840
agttcaagcc acgatcattt ttcagtcctg gcactggcca gaggagtgaa cgctagcgca    6900
acagtgaatg tcactgtgag ggccctgctg cacgtgtggg ctggaggccc ttggccacag    6960
ggagccacac tgcgactgga ccctactgtg ctggatgcag agagctggc aaatcgaacc    7020
ggcagcgtgc cacgattccg gctgctggca ggacctcgac atggacgagt ggtccgggtg    7080
ccaagagcta ggactgagcc cggcggcagc cagctggtgg aacagtttac ccagcaggac    7140
ctggaggatg ggcggctggg actggaagtg ggaggcctg agggacgagc tccaggacct    7200
gcagggggaca gtctgacact ggagctgtgg gcacaggag tgcctcccgc agtggcttca    7260
ctggatttcg ctactgaacc ttacaacgcc gctagaccat atagtgtcgc cctgctgtca    7320
gtgccagaag cagccaggac tgaggctggg aaacccgaat cctctactcc taccggagag    7380
ccaggcccca tggctagttc acctgtgcca accgtcgcaa agggcgggtt cctgggattt    7440
```

```
ctggaggcca atatgttcag cgtgatcatt ccagtgtgcc tggtcctgct gctgctggcc    7500
ctgatcctgc ccctgctgtt ttacctgcgc aagcgaaaca aagccggaaa gcacgacgtg    7560
caggtgctgg ctgcaaaacc tagaaatggg ctggccggag atgcagaggc cttcaggaag    7620
gtggaaccag gccaggctat tcccctggcc gctgtgcctg ggcagggagc agccgctgga    7680
ggccaggccg acccagagct gctgcagttt tgtagagccc ctaatcccgc cctgaagaat    7740
ggacagtatt gggtctgata actcgagtct agagggcccg tttaaacccg ctgatcagcc    7800
tcgactgtgc cttctagttg ccagccatct gttgtttgcc cctcccccgt gccttccttg    7860
accctggaag gtgccactcc cactgtcctt tcctaataaa atgaggaaat tgcatcgcat    7920
tgtctgagta ggtgtcattc tattctgggg ggtggggtgg ggcaggacag caaggggag     7980 gattgggaag acaatagcag gcatgctggg gatgcggtgg gctctatggc ttctactggg    8040
cggttttatg gacagcaagc gaaccggaat tgccagctgg ggcgccctct ggtaaggttg    8100
ggaagccctg caaagtaaac tggatggctt tcttgccgcc aaggatctga tggcgcaggg    8160
gatcaagctc tgatcaagag acaggatgag gatcgtttcg catgattgaa caagatggat    8220
tgcacgcagg ttctccggcc gcttgggtgg agaggctatt cggctatgac tgggcacaac    8280
agacaatcgg ctgctctgat gccgccgtgt tccggctgtc agcgcagggg cgcccggttc    8340
tttttgtcaa gaccgacctg tccggtgccc tgaatgaact gcaagacgag gcagcgcggc    8400
tatcgtggct ggccacgacg ggcgttcctt gcgcagctgt gctcgacgtt gtcactgaag    8460
cgggaaggga ctggctgcta ttgggcgaag tgccggggca ggatctcctg tcatctcacc    8520
ttgctcctgc cgagaaagta tccatcatgg ctgatgcaat gcggcggctg catacgcttg    8580
atccggctac ctgcccattc gaccaccaag cgaaacatcg catcgagcga gcacgtactc    8640
ggatggaagc cggtcttgtc gatcaggatg atctggacga agagcatcag gggctcgcgc    8700
cagccgaact gttcgccagg ctcaaggcga gcatgcccga cggcgaggat ctcgtcgtga    8760
cccatggcga tgcctgcttg ccgaatatca tggtggaaaa tggccgcttt tctggattca    8820
tcgactgtgg ccggctgggt gtggcggacc gctatcagga catagcgttg gctacccgtg    8880
atattgctga agagcttggc ggcgaatggg ctgaccgctt cctcgtgctt tacggtatcg    8940
ccgctcccga ttcgcagcgc atcgccttct atcgccttct tgacgagttc ttctgaatta    9000
ttaacgctta caatttcctg atgcggtatt ttctccttac gcatctgtgc ggtatttcac    9060
accgcatcag gtggcacttt tcggggaaat gtgcgcggaa cccctatttg tttattttc    9120 taaatacatt caaatatgta tccgctcatg agacaataac cctgataaat gcttcaataa    9180
tagcacgtgc taaaacttca ttttaattt aaaaggatct aggtgaagat cctttttgat    9240
aatctcatga ccaaaatccc ttaacgtgag ttttcgttcc actgagcgtc agaccccgta    9300
gaaaagatca aggatcttc ttgagatcct ttttttctgc gcgtaatctg ctgcttgcaa    9360
acaaaaaaac caccgctacc agcggtggtt tgtttgccgg atcaagagct accaactctt    9420
tttccgaagg taactggctt cagcagagcg cagataccaa atactgttct tctagtgtag    9480
ccgtagttag gccaccactt caagaactct gtagcaccgc ctacatacct cgctctgcta    9540
atcctgttac cagtggctgc tgccagtggc gataagtcgt gtcttaccgg gttggactca    9600
agacgatagt taccggataa ggcgcagcgg tcgggctgaa cggggggttc gtgcacacag    9660
cccagcttgg agcgaacgac ctacaccgaa ctgagatacc tacagcgtga gctatgagaa    9720
agcgccacgc ttcccgaagg gagaaaggcg gacaggtatc cggtaagcgg cagggtcgga    9780
```

```
                                        -continued
acaggagagc gcacgaggga gcttccaggg ggaaacgcct ggtatcttta tagtcctgtc    9840
gggtttcgcc acctctgact tgagcgtcga tttttgtgat gctcgtcagg ggggcggagc    9900
ctatggaaaa acgccagcaa cgcggcctttt ttacggttcc tggccttttg ctggcctttt   9960
gctcacatgt tctt                                                      9974
```